United States Patent
Power et al.

(10) Patent No.: US 9,534,054 B2
(45) Date of Patent: Jan. 3, 2017

(54) MONOCLONAL ANTIBODY DIRECTED AGAINST CXCR5

(71) Applicant: ARES TRADING S.A., Aubonne (CH)

(72) Inventors: Christine Power, Thoiry (FR); Olivier Leger, Saint-Sixt (FR); Paul Bradfield, Geneva (CH); Horacio G. Nastri, Armonk, NY (US); Christel Iffland, Arlington, MA (US); Qi An, Nashua, NH (US)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 14/787,478

(22) PCT Filed: Apr. 30, 2014

(86) PCT No.: PCT/EP2014/058903
§ 371 (c)(1),
(2) Date: Oct. 28, 2015

(87) PCT Pub. No.: WO2014/177652
PCT Pub. Date: Nov. 6, 2014

(65) Prior Publication Data
US 2016/0115235 A1    Apr. 28, 2016

(30) Foreign Application Priority Data
May 2, 2013   (EP) .................................. 13166251

(51) Int. Cl.
*A61K 39/00* (2006.01)
*A61K 39/395* (2006.01)
*A61K 51/10* (2006.01)
*C07K 16/28* (2006.01)

(52) U.S. Cl.
CPC ........... *C07K 16/2866* (2013.01); *A61K 39/00* (2013.01); *A61K 39/395* (2013.01); *A61K 2039/505* (2013.01); *C07K 2317/21* (2013.01); *C07K 2317/55* (2013.01); *C07K 2317/565* (2013.01); *C07K 2317/567* (2013.01); *C07K 2317/732* (2013.01); *C07K 2317/76* (2013.01); *C07K 2317/92* (2013.01)

(58) Field of Classification Search
CPC .............. A61K 2039/505; A61K 39/00; A61K 51/1027; C07K 2317/92; C07K 2317/76; C07K 2317/565; C07K 2317/732; C07K 16/28; C07K 16/2866
See application file for complete search history.

(56) References Cited

U.S. PATENT DOCUMENTS
2012/0128688 A1    5/2012   Lillard et al.

FOREIGN PATENT DOCUMENTS
WO   WO 2009/032661   3/2009
WO   WO 2012/010582   1/2012

OTHER PUBLICATIONS

Bürkle, A., et al., "Overexpression of the CXCR5 chemokine receptor, and its ligand, CXCL13 in B-cell chronic lymphocytic leukemia," *Blood*, Nov. 1, 2007, vol. 110, No. 9, pp. 3316-3325.
Del Grosso, F., et al., "Role of CXCL13-CXCR5 Crosstalk Between Malignant Neuroblastoma Cells and Schwannian Stromal Cells in Neuroblastic Tumors," *Molecular Cancer Research*, Jun. 3, 2011, vol. 9, No. 7, pp. 815-823.
"Anti-CXCR5 (C-X-C Chemokine Receptor 5) Antibodies—Antibody Search," Jan. 1, 2011, pp. 1-8, XP002654954, retrieved from Internet on Aug. 1, 2011: URL: http://www.biocompare.com/ProductListings/3194/CXCR5-C-X-C-Chemokine-Receptor-5.htm]?types=6-53252.
Written Opinion in International Application No. PCT/EP2014/058903, Sep. 1, 2014, pp. 1-7.

*Primary Examiner* — Robert Landsman
*Assistant Examiner* — Bruce D Hissong
(74) *Attorney, Agent, or Firm* — Saliwanchik, Lloyd & Eisenschenk

(57) ABSTRACT

The invention relates to monoclonal antibodies against human CXCR5 and to their use in the treatment of autoimmune or inflammatory diseases, as well as cancers.

20 Claims, 13 Drawing Sheets

```
             <-------------FWR1-----------><DR1><-----FWR2---><------CDR2----->
40C01-VH     EVQLLESGGGLVQPGGSLRLSCAASGFTFSRYVMVWVRQAPGKGLDWVSGISPSGGVTRYADSVKG
IGHV3-23*01  .............................S.A.S..........E...A..G...S.Y.......
40C01-VH1    .............................................E................A....
40C01-VH2    .............................S...............E................A....

<--------------FWR3-------------><-----CDR3---><--FWR4--->
40C01-VH     RFTISRDNSKNTLYLQMNSLRAEDTAMYYCARIRKEMTTISYFFDYWGQGTLVTVSS
IGHV3-23*01  ..........................V....K
IGHJ4*02                                     Y..............
40C01-VH1    ..........................V.............................
40C01-VH2    ..........................V........K....................
```

Figure 1

```
             <---------FWR1--------><---CDR1--><-----FWR2----><-CDR2>
40C01-Vk     DIQMTRAPDSLSASVGDRVTITCRASQGVDIYVAWYQQKPGKAPKLLMHSASTLAS
IGKV1-27*01  .....QS.S....................ISN.L.........V....IYA....Q.
40C01-Vk1    .....KS.S....................A.............V....IY.T.....
40C01-Vk2    .....QS.S....................A.............V....IY.T.....
40C01-Vk3    .....QS.S....................A.............V....IY.T.....

<--------------FWR3-------------><--CDR3-><--FWR4-->
40C01-VL     GVPSRFSGRGSGTDFTLTINSLQAEDVATYYCQSHNSAVVTFGQGTRLEIK
IGKV1-27*01  ........S...........S...P.........KY...
IGKJ5*01                                            I...........
40C01-Vk1    ........S...........S...P..............
40C01-Vk2    ........S...........S...P..............
40C01-Vk3    ........S...........S...P..........A...
```

Figure 2

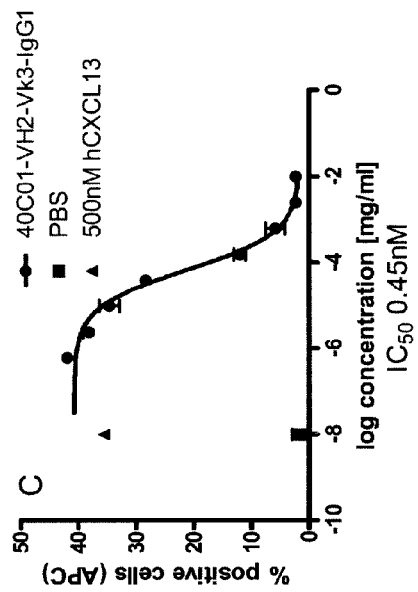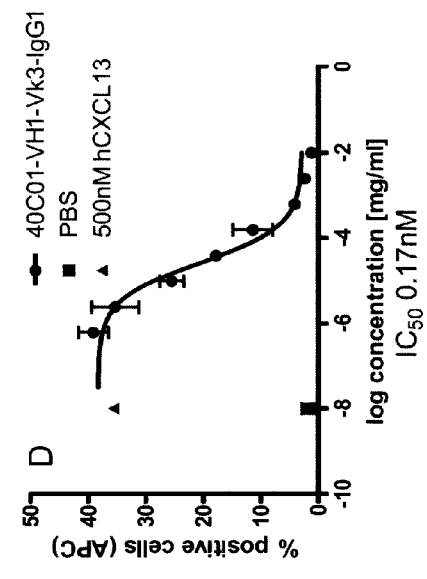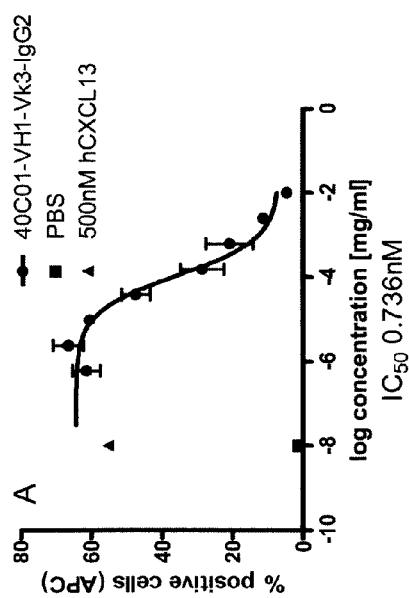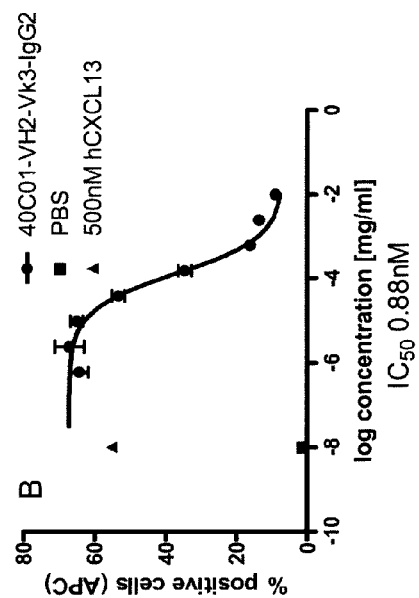
Figure 10a
Figure 10b
Figure 10c
Figure 10d

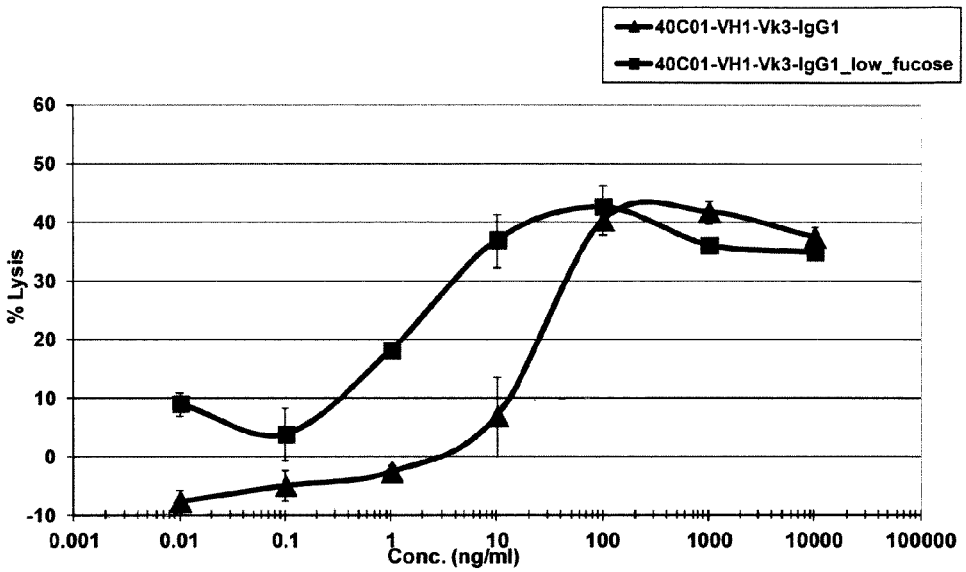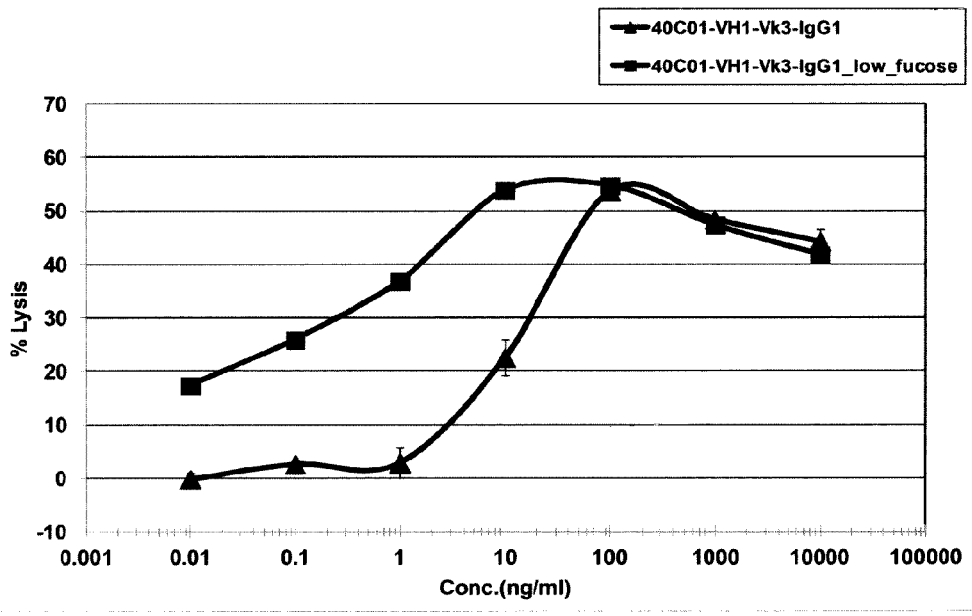
Figure 15

SEQUENCE LISTING

<160> NUMBER OF SEQ ID NOS: 85

<210> SEQ ID NO 1
<211> LENGTH: 123
<212> TYPE: PRT
<213> ORGANISM: artificial sequence
<220> FEATURE:
<223> OTHER INFORMATION: Variable heavy chain for the mAbs 40C01 and 12A01

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Val Trp Val Arg Gln Ala Pro Gly Lys Gly Leu Asp Trp Val
        35                  40                  45

Ser Gly Ile Ser Pro Ser Gly Val Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Ile Arg Lys Glu Met Thr Thr Ile Ser Tyr Phe Phe Asp Tyr
            100                 105                 110

Trp Gly Gln Gly Thr Leu Val Thr Val Ser Ser
        115                 120

<210> SEQ ID NO 2
<211> LENGTH: 107
<212> TYPE: PRT
<213> ORGANISM: artificial sequence
<220> FEATURE:
<223> OTHER INFORMATION: Variable light chain for the mAb 40C01

<400> SEQUENCE: 2

Asp Ile Gln Met Thr Arg Ala Pro Asp Ser Leu Ser Ala Ser Val Gly
1               5                   10                  15

Asp Arg Val Thr Ile Thr Cys Arg Ala Ser Gln Gly Val Asp Ile Tyr
            20                  25                  30

Val Ala Trp Tyr Gln Gln Lys Pro Gly Lys Ala Pro Lys Leu Leu Met
        35                  40                  45

His Ser Ala Ser Thr Leu Ala Ser Gly Val Pro Ser Arg Phe Ser Gly
    50                  55                  60

Arg Gly Ser Gly Thr Asp Phe Thr Leu Thr Ile Asn Ser Leu Gln Ala
65                  70                  75                  80

Glu Asp Val Ala Thr Tyr Tyr Cys Gln Ser His Asn Ser Ala Val Val
                85                  90                  95

Thr Phe Gly Gln Gly Thr Arg Leu Glu Ile Lys
            100                 105

<210> SEQ ID NO 3
<211> LENGTH: 123
<212> TYPE: PRT
<213> ORGANISM: artificial sequence
<220> FEATURE:
<223> OTHER INFORMATION: Variable heavy chain for the mAb 40C01-VH1

<400> SEQUENCE: 3

Glu Val Gln Leu Leu Glu Ser Gly Gly Gly Leu Val Gln Pro Gly Gly

```
1               5                   10                  15
Ser Leu Arg Leu Ser Cys Ala Ala Ser Gly Phe Thr Phe Ser Arg Tyr
            20                  25                  30

Val Met Val Trp Val Arg Gln Ala Pro Gly Lys Gly Leu Glu Trp Val
            35                  40                  45

Ser Gly Ile Ser Pro Ser Gly Gly Val Thr Arg Tyr Ala Ala Ser Val
            50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Arg Ile Arg Lys Glu Met Thr Thr Ile Ser Tyr Phe Phe Asp Tyr
                100                 105                 110

Trp Gly Gln Gly Thr Leu Val Thr Val Ser Ser
                115                 120
```

<210> SEQ ID NO 4
<211> LENGTH: 123
<212> TYPE: PRT
<213> ORGANISM: artificial sequence
<220> FEATURE:
<223> OTHER INFORMATION: Variable heavy chain for the mAb 40C01-VH2

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Ser
            20                  25                  30

Val Met Val Trp Val Arg Gln Ala Pro Gly Lys Gly Leu Glu Trp Val
            35                  40                  45

Ser Gly Ile Ser Pro Ser Gly Gly Val Thr Arg Tyr Ala Ala Ser Val
            50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Arg Ile Arg Lys Glu Lys Thr Thr Ile Ser Tyr Phe Phe Asp Tyr
                100                 105                 110

Trp Gly Gln Gly Thr Leu Val Thr Val Ser Ser
                115                 120
```

<210> SEQ ID NO 5
<211> LENGTH: 107
<212> TYPE: PRT
<213> ORGANISM: artificial sequence
<220> FEATURE:
<223> OTHER INFORMATION: Variable light chain for the mAb 40C01-Vk1

<400> SEQUENCE: 5

```
Asp Ile Gln Met Thr Lys Ser Pro Ser Ser Leu Ser Ala Ser Val Gly
1               5                   10                  15

Asp Arg Val Thr Ile Thr Cys Arg Ala Ser Gln Gly Val Asp Ala Tyr
            20                  25                  30

Val Ala Trp Tyr Gln Gln Lys Pro Gly Lys Ala Pro Lys Leu Leu Ile
            35                  40                  45

Tyr Ser Thr Ser Thr Leu Ala Ser Gly Val Pro Ser Arg Phe Ser Gly
            50                  55                  60
```

```
Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser His Asn Ser Ala Val Val
                85                  90                  95

Thr Phe Gly Gln Gly Thr Arg Leu Glu Ile Lys
            100                 105
```

<210> SEQ ID NO 6
<211> LENGTH: 107
<212> TYPE: PRT
<213> ORGANISM: artificial sequence
<220> FEATURE:
<223> OTHER INFORMATION: Variable light chain for the mAb 40C01-Vk2

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Asp Ala Tyr
                20                  25                  30

Val Ala Trp Tyr Gln Gln Lys Pro Gly Lys Val Pro Lys Leu Leu Ile
            35                  40                  45

Tyr Ser Thr Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser His Asn Ser Ala Val Val
                85                  90                  95

Thr Phe Gly Gln Gly Thr Arg Leu Glu Ile Lys
            100                 105
```

<210> SEQ ID NO 7
<211> LENGTH: 107
<212> TYPE: PRT
<213> ORGANISM: artificial sequence
<220> FEATURE:
<223> OTHER INFORMATION: Variable light chain for the mAb 40C01-Vk3

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Asp Ala Tyr
                20                  25                  30

Val Ala Trp Tyr Gln Gln Lys Pro Gly Lys Val Pro Lys Leu Leu Ile
            35                  40                  45

Tyr Ser Thr Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser His Asn Ala Ala Val Val
                85                  90                  95

Thr Phe Gly Gln Gly Thr Arg Leu Glu Ile Lys
            100                 105
```

<210> SEQ ID NO 8
<211> LENGTH: 5
<212> TYPE: PRT
<213> ORGANISM: artificial sequence
<220> FEATURE:
<223> OTHER INFORMATION: CDR1, heavy chain

```
<400> SEQUENCE: 8

Arg Tyr Val Met Val
1               5

<210> SEQ ID NO 9
<211> LENGTH: 5
<212> TYPE: PRT
<213> ORGANISM: artificial sequence
<220> FEATURE:
<223> OTHER INFORMATION: CDR1, heavy chain

<400> SEQUENCE: 9

Arg Ser Val Met Val
1               5

<210> SEQ ID NO 10
<211> LENGTH: 17
<212> TYPE: PRT
<213> ORGANISM: artificial sequence
<220> FEATURE:
<223> OTHER INFORMATION: CDR2, heavy chain

<400> SEQUENCE: 10

Gly Ile Ser Pro Ser Gly Gly Val Thr Arg Tyr Ala Asp Ser Val Lys
1               5                   10                  15

Gly

<210> SEQ ID NO 11
<211> LENGTH: 17
<212> TYPE: PRT
<213> ORGANISM: artificial sequence
<220> FEATURE:
<223> OTHER INFORMATION: CDR2, heavy chain

<400> SEQUENCE: 11

Gly Ile Ser Pro Ser Gly Gly Val Thr Arg Tyr Ala Ala Ser Val Lys
1               5                   10                  15

Gly

<210> SEQ ID NO 12
<211> LENGTH: 14
<212> TYPE: PRT
<213> ORGANISM: artificial sequence
<220> FEATURE:
<223> OTHER INFORMATION: CDR3, heavy chain

<400> SEQUENCE: 12

Ile Arg Lys Glu Met Thr Thr Ile Ser Tyr Phe Phe Asp Tyr
1               5                   10

<210> SEQ ID NO 13
<211> LENGTH: 14
<212> TYPE: PRT
<213> ORGANISM: artificial sequence
<220> FEATURE:
<223> OTHER INFORMATION: CDR3, heavy chain

<400> SEQUENCE: 13

Ile Arg Lys Glu Lys Thr Thr Ile Ser Tyr Phe Phe Asp Tyr
1               5                   10

<210> SEQ ID NO 14
<211> LENGTH: 11
<212> TYPE: PRT
<213> ORGANISM: artificial sequence
```

```
<220> FEATURE:
<223> OTHER INFORMATION: CDR1, light chain

<400> SEQUENCE: 14

Arg Ala Ser Gln Gly Val Asp Ile Tyr Val Ala
1               5                   10

<210> SEQ ID NO 15
<211> LENGTH: 11
<212> TYPE: PRT
<213> ORGANISM: artificial sequence
<220> FEATURE:
<223> OTHER INFORMATION: CDR1, light chain

<400> SEQUENCE: 15

Arg Ala Ser Gln Gly Val Asp Ala Tyr Val Ala
1               5                   10

<210> SEQ ID NO 16
<211> LENGTH: 7
<212> TYPE: PRT
<213> ORGANISM: artificial sequence
<220> FEATURE:
<223> OTHER INFORMATION: CDR2, light chain

<400> SEQUENCE: 16

Ser Ala Ser Thr Leu Ala Ser
1               5

<210> SEQ ID NO 17
<211> LENGTH: 7
<212> TYPE: PRT
<213> ORGANISM: artificial sequence
<220> FEATURE:
<223> OTHER INFORMATION: CDR2, light chain

<400> SEQUENCE: 17

Ser Thr Ser Thr Leu Ala Ser
1               5

<210> SEQ ID NO 18
<211> LENGTH: 9
<212> TYPE: PRT
<213> ORGANISM: artificial sequence
<220> FEATURE:
<223> OTHER INFORMATION: CDR3, light chain

<400> SEQUENCE: 18

Gln Ser His Asn Ser Ala Val Val Thr
1               5

<210> SEQ ID NO 19
<211> LENGTH: 9
<212> TYPE: PRT
<213> ORGANISM: artificial sequence
<220> FEATURE:
<223> OTHER INFORMATION: CDR3, light chain

<400> SEQUENCE: 19

Gln Ser His Asn Ala Ala Val Val Thr
1               5

<210> SEQ ID NO 20
<211> LENGTH: 30
<212> TYPE: PRT
<213> ORGANISM: artificial sequence
<220> FEATURE:
```

<223> OTHER INFORMATION: FR1, heavy chain

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 21
<211> LENGTH: 14
<212> TYPE: PRT
<213> ORGANISM: artificial sequence
<220> FEATURE:
<223> OTHER INFORMATION: FR2, heavy chain

<400> SEQUENCE: 21

Trp Val Arg Gln Ala Pro Gly Lys Gly Leu Asp Trp Val Ser
1               5                   10

<210> SEQ ID NO 22
<211> LENGTH: 14
<212> TYPE: PRT
<213> ORGANISM: artificial sequence
<220> FEATURE:
<223> OTHER INFORMATION: FR2, heavy chain

<400> SEQUENCE: 22

Trp Val Arg Gln Ala Pro Gly Lys Gly Leu Glu Trp Val Ser
1               5                   10

<210> SEQ ID NO 23
<211> LENGTH: 32
<212> TYPE: PRT
<213> ORGANISM: artificial sequence
<220> FEATURE:
<223> OTHER INFORMATION: FR3, heavy chain

<400> SEQUENCE: 23

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Arg
            20                  25                  30

<210> SEQ ID NO 24
<211> LENGTH: 32
<212> TYPE: PRT
<213> ORGANISM: artificial sequence
<220> FEATURE:
<223> OTHER INFORMATION: FR3, heavy chain

<400> SEQUENCE: 24

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 25
<211> LENGTH: 9
<212> TYPE: PRT
<213> ORGANISM: artificial sequence
<220> FEATURE:
<223> OTHER INFORMATION: FR4, heavy chain

<400> SEQUENCE: 25

Tyr Trp Gly Gln Gly Thr Leu Val Thr

```
1               5

<210> SEQ ID NO 26
<211> LENGTH: 23
<212> TYPE: PRT
<213> ORGANISM: artificial sequence
<220> FEATURE:
<223> OTHER INFORMATION: FR1, light chain

<400> SEQUENCE: 26

Asp Ile Gln Met Thr Arg Ala Pro Asp Ser Leu Ser Ala Ser Val Gly
1               5                   10                  15

Asp Arg Val Thr Ile Thr Cys
            20

<210> SEQ ID NO 27
<211> LENGTH: 23
<212> TYPE: PRT
<213> ORGANISM: artificial sequence
<220> FEATURE:
<223> OTHER INFORMATION: FR1, light chain

<400> SEQUENCE: 27

Asp Ile Gln Met Thr Lys Ser Pro Ser Ser Leu Ser Ala Ser Val Gly
1               5                   10                  15

Asp Arg Val Thr Ile Thr Cys
            20

<210> SEQ ID NO 28
<211> LENGTH: 23
<212> TYPE: PRT
<213> ORGANISM: artificial sequence
<220> FEATURE:
<223> OTHER INFORMATION: FR1, light chain

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 15
<212> TYPE: PRT
<213> ORGANISM: artificial sequence
<220> FEATURE:
<223> OTHER INFORMATION: FR2, light chain

<400> SEQUENCE: 29

Trp Tyr Gln Gln Lys Pro Gly Lys Ala Pro Lys Leu Leu Met His
1               5                   10                  15

<210> SEQ ID NO 30
<211> LENGTH: 15
<212> TYPE: PRT
<213> ORGANISM: artificial sequence
<220> FEATURE:
<223> OTHER INFORMATION: FR2, light chain

<400> SEQUENCE: 30

Trp Tyr Gln Gln Lys Pro Gly Lys Ala Pro Lys Leu Leu Ile Tyr
1               5                   10                  15

<210> SEQ ID NO 31
<211> LENGTH: 15
```

```
<212> TYPE: PRT
<213> ORGANISM: artificial sequence
<220> FEATURE:
<223> OTHER INFORMATION: FR2, light chain

<400> SEQUENCE: 31

Trp Tyr Gln Gln Lys Pro Gly Lys Val Pro Lys Leu Leu Ile Tyr
1               5                   10                  15

<210> SEQ ID NO 32
<211> LENGTH: 32
<212> TYPE: PRT
<213> ORGANISM: artificial sequence
<220> FEATURE:
<223> OTHER INFORMATION: FR3, light chain

<400> SEQUENCE: 32

Gly Val Pro Ser Arg Phe Ser Gly Arg Gly Ser Gly Thr Asp Phe Thr
1               5                   10                  15

Leu Thr Ile Asn Ser Leu Gln Ala Glu Asp Val Ala Thr Tyr Tyr Cys
            20                  25                  30

<210> SEQ ID NO 33
<211> LENGTH: 32
<212> TYPE: PRT
<213> ORGANISM: artificial sequence
<220> FEATURE:
<223> OTHER INFORMATION: FR3, light chain

<400> SEQUENCE: 33

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 34
<211> LENGTH: 10
<212> TYPE: PRT
<213> ORGANISM: artificial sequence
<220> FEATURE:
<223> OTHER INFORMATION: FR4, light chain

<400> SEQUENCE: 34

Phe Gly Gln Gly Thr Arg Leu Glu Ile Lys
1               5                   10

<210> SEQ ID NO 35
<211> LENGTH: 372
<212> TYPE: PRT
<213> ORGANISM: homo sapiens
<220> FEATURE:
<223> OTHER INFORMATION: Human CXCR5

<400> SEQUENCE: 35

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80
```

```
Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 36
<211> LENGTH: 372
<212> TYPE: PRT
<213> ORGANISM: Macaca fascicularis
<220> FEATURE:
<223> OTHER INFORMATION: Macaca fascicularis CXCR5

<400> SEQUENCE: 36

Met Asn Tyr Pro Leu Thr Leu Glu Met Asp Leu Glu Asn Leu Glu Asp
1               5                   10                  15

Leu Phe Leu Glu Phe Asp Lys Phe Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60
```

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Phe Ala Leu Pro Glu Ile Leu Phe Ala Lys Val Ser Gln
            180                 185                 190

Ala His Pro Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Val Arg Leu Lys
        275                 280                 285

Ala Val Asp Asn Thr Cys Glu Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Lys Ser Ser Leu Ser Glu Ser Glu Asn Ala Thr Ser
        355                 360                 365

Leu Thr Thr Phe
    370

<210> SEQ ID NO 37
<211> LENGTH: 372
<212> TYPE: PRT
<213> ORGANISM: Macaca mulatta
<220> FEATURE:
<223> OTHER INFORMATION: Macaca mulatta CXCR5

<400> SEQUENCE: 37

Met Asn Tyr Pro Leu Met Leu Glu Met Asp Leu Glu Asn Leu Glu Asp
1               5                   10                  15

Leu Phe Leu Glu Phe Asp Lys Phe Asp Asn Tyr Asn Asp Thr Ser Leu
            20                  25                  30

Val Glu Asn His Leu Cys Pro Ala Thr Glu Gly Pro Leu Met Ala Ser
        35                  40                  45

```
Phe Lys Ala Val Phe Val Pro Val Ala Tyr Ser Leu Ile Phe Leu Leu
         50                  55                  60

Gly Val Ile Gly Asn Val Leu Val Leu Val Ile Leu Glu Arg His Arg
 65                  70                  75                  80

Gln Thr Arg Ser Ser Thr Glu Thr Phe Leu Phe His Leu Ala Val Ala
                 85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Phe Ala Leu Pro Glu Ile Leu Phe Ala Lys Val Ser Gln
            180                 185                 190

Ala His Pro Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Val Arg Leu Lys
        275                 280                 285

Ala Val Asp Asn Thr Cys Glu Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Lys Ser Ser Leu Ser Glu Ser Glu Asn Ala Thr Ser
        355                 360                 365

Leu Thr Thr Phe
    370

<210> SEQ ID NO 38
<211> LENGTH: 329
<212> TYPE: PRT
<213> ORGANISM: homo sapiens
<220> FEATURE:
<223> OTHER INFORMATION: Heavy chain constant region - human IgG1,
      allotype G1m(f)

<400> SEQUENCE: 38

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
```

```
                    20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 39
<211> LENGTH: 328
<212> TYPE: PRT
<213> ORGANISM: homo sapiens
<220> FEATURE:
<223> OTHER INFORMATION: Heavy chain constant region - human IgG2
      DI-NQ-HC2h subtype

<400> SEQUENCE: 39

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Pro Lys Ser Ser Asp Lys Thr His Thr Cys Pro Pro Cys
            100                 105                 110

Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Ala Gln Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
            195                 200                 205

Gly Leu Pro Ala Pro Ile Glu Lys Thr Ile Ser Lys Thr Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 40
<211> LENGTH: 326
<212> TYPE: PRT
<213> ORGANISM: homo sapiens
<220> FEATURE:
<223> OTHER INFORMATION: Heavy chain constant region - human IgG4
      S228P-R409K subtype

<400> SEQUENCE: 40

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
 65                  70                  75                  80

-continued

```
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Lys Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 41
<211> LENGTH: 429
<212> TYPE: DNA
<213> ORGANISM: artificial sequence
<220> FEATURE:
<223> OTHER INFORMATION: Variable heavy chain for mAbs 40C01 and 12A01

<400> SEQUENCE: 41
atggagaccg acaccctgct gctgtgggtg ctgctgctgt gggtgcccgg gtcgaccggc      60
gaagttcaat tgttagagtc tggtggcggt cttgttcagc ctggtggttc tttacgtctt     120
tcttgcgctg cttccggatt cactttctct cgttacgtta tggtttgggt cgccaagct     180 cctggtaaag gtttgattg gtttctggt atctctcctt ctggtggcgt tactcgttat     240
gctgactccg ttaaaggtcg cttcactatc tctagagaca actctaagaa tactctctac     300
ttgcagatga acagcttaag ggctgaggac accgccatgt attactgtgc acggatacga     360
aaggagatga ctacaatttc gtacttcttt gactactggg gccagggcac cctggtcacc     420
gtctcaagc                                                             429

<210> SEQ ID NO 42
<211> LENGTH: 381
<212> TYPE: DNA
```

```
<213> ORGANISM: artificial sequence
<220> FEATURE:
<223> OTHER INFORMATION: Variable light chain for the mAb 40C01

<400> SEQUENCE: 42
atggagaccg acaccctgct gctgtgggtg ctgctgctgt gggtgcccgg gtcgaccggt      60
gacatccaga tgacccgggc accagactcc ctgtctgcct ctgtaggaga cagagtcacc     120
atcacttgcc gggcgagtca gggcgttgac atttatgttg cctggtatca gcagaaaccg     180
ggaaaagccc ctaaactcct gatgcatagt gcatccactt tggcatcagg ggtcccatct     240
cgcttcagtg gtcgtggatc tgggacggac ttcactctca ccatcaacag cctgcaggct     300
gaagatgttg ccacttacta ctgtcaaagt cataacagtc ccgtcgtcac tttcggccaa     360
gggacacgac tggagattaa a                                               381

<210> SEQ ID NO 43
<211> LENGTH: 426
<212> TYPE: DNA
<213> ORGANISM: artificial sequence
<220> FEATURE:
<223> OTHER INFORMATION: Variable heavy chain for the mAb 40C01-VH1

<400> SEQUENCE: 43
atggaatggt cctgggtgtt cctgttcttc ctgtccgtga ccaccggcgt gcactccgag      60
gtgcagctgc tggaatctgg ggggggactg gtgcagcctg cggctccct gagactgtct      120 tgcgccgcct ccggcttcac cttctccaga tacgtgatgg tctgggtccg acaggcccct     180
ggcaagggcc tggaatgggt gtccggcatc tctcccagtg gcggcgtgac cagatacgcc     240
gcctctgtga agggccggtt caccatctcc cgggacaact ccaagaacac cctgtacctg     300
cagatgaact ccctgcgggc cgaggacacc gccgtgtact actgcgcccg gatcagaaaa     360
gagatgacca ccatctccta ctttttcgac tactggggcc agggcaccct ggtgacagtg     420
tcctcc                                                                426

<210> SEQ ID NO 44
<211> LENGTH: 426
<212> TYPE: DNA
<213> ORGANISM: artificial sequence
<220> FEATURE:
<223> OTHER INFORMATION: Variable heavy chain for the mAb 40C01-VH1
      (codon optimized sequence)

<400> SEQUENCE: 44
atggaatggt cctgggtgtt cctgttcttc ctgtccgtga ccaccggcgt gcactccgag      60
gtgcagctgc tggaatctgg gggcggactg gtgcagcctg cggctccct gagactgtct     120 tgcgccgcct ccggcttcac cttctccaga tacgtgatgg tctgggtccg acaggcccct     180
ggcaagggcc tggaatgggt gtccggcatc tctcccagtg gcggcgtgac cagatacgcc     240
gcctctgtga agggccggtt caccatctcc cgggacaact ccaagaacac cctgtacctg     300
cagatgaact ccctgcgggc cgaggacacc gccgtgtact actgcgcccg gatcagaaaa     360
gagatgacca ccatctccta ctttttcgac tactggggcc agggcaccct ggtgacagtg     420
tcctcc                                                                426

<210> SEQ ID NO 45
<211> LENGTH: 426
<212> TYPE: DNA
<213> ORGANISM: artificial sequence
<220> FEATURE:
```

<223> OTHER INFORMATION: Variable heavy chain for the mAb 40C01-VH2

<400> SEQUENCE: 45

```
atggaatggt cctgggtgtt cctgttcttc ctgtccgtga ccaccggcgt gcactccgag    60
gtgcagctgc tggaatctgg ggcggactg gtgcagcctg cggctccct gagactgtct   120
tgcgccgcct ccggcttcac cttctccaga tccgtgatgg tctgggtccg acaggcccct   180
ggcaagggcc tggaatgggt gtccggcatc tctcccagtg cggcgtgac cagatacgcc   240
gcctctgtga agggccggtt caccatctcc cgggacaact ccaagaacac cctgtacctg   300
cagatgaact ccctgcgggc cgaggacacc gccgtgtact actgcgcccg gatcagaaaa   360
gagaagacca ccatctccta cttttttcgac tactggggcc agggcaccct ggtgacagtg   420
tcctcc                                                               426
```

<210> SEQ ID NO 46
<211> LENGTH: 426
<212> TYPE: DNA
<213> ORGANISM: artificial sequence
<220> FEATURE:
<223> OTHER INFORMATION: Variable heavy chain for the mAb 40C01-VH2
    (codon optimized sequence)

<400> SEQUENCE: 46

```
atggaatggt cctgggtgtt cctgttcttc ctgagcgtga ccaccggcgt gcacagcgag    60
gtgcagctgc tggaaagcgg cggaggactg gtgcagcctg aggcagcct gagactgtct   120
tgcgccgcca gcggcttcac cttcagcaga tccgtgatgg tgtgggtgcg ccaggccct   180
ggcaagggac tggagtgggt gtccggcatc agccctctg gcgcgtgac cagatacgcc   240
gccagcgtga agggccggtt caccatcagc cgggacaaca gcaagaacac cctgtacctg   300
cagatgaaca gcctgcgggc cgaggacacc gccgtgtact actgcgccag aatccggaaa   360
gagaagacca ccatcagcta cttttttcgac tactggggac agggcaccct ggtgacagtg   420
tccagc                                                               426
```

<210> SEQ ID NO 47
<211> LENGTH: 381
<212> TYPE: DNA
<213> ORGANISM: artificial sequence
<220> FEATURE:
<223> OTHER INFORMATION: Variable light chain for the mAb 40C01-Vk1

<400> SEQUENCE: 47

```
atggagaccg acaccctgct gctgtgggtg ctgctgctgt gggtgcccgg gtcgaccggt    60
gacatccaga tgaccaagtc cccaagctcc ctgtctgcct ctgtaggaga cagagtcacc   120
atcacttgcc gggcgagtca gggcgttgac gcttatgttg cctggtatca gcagaaaccg   180
ggaaaagccc ctaaactcct gatctacagt acatccactt tggcatcagg ggtcccatct   240
cgcttcagtg gtagtggatc tgggacggac ttcactctca ccatcagcag cctgcagcct   300
gaagattttg ccacttacta ctgtcaaagt cataacagtg ccgtcgtcac tttcggccaa   360
gggacacgac tggagattaa a                                              381
```

<210> SEQ ID NO 48
<211> LENGTH: 381
<212> TYPE: DNA
<213> ORGANISM: artificial sequence
<220> FEATURE:
<223> OTHER INFORMATION: Variable light chain for the mAb 40C01-Vk2

```
<400> SEQUENCE: 48
atggagaccg acaccctgct gctgtgggtg ctgctgctgt gggtgcccgg gtcgaccggt    60
gacatccaga tgacccagtc cccaagctcc ctgtctgcct ctgtaggaga cagagtcacc   120
atcacttgcc gggcgagtca gggcgttgac gcttatgttg cctggtatca gcagaaaccg   180
ggaaaagtcc ctaaactcct gatctacagt acatccactt tggcatcagg ggtcccatct   240
cgcttcagtg gtagtggatc tgggacggac ttcactctca ccatcagcag cctgcagcct   300
gaagatgtgg ccacttacta ctgtcaaagt cataacagtg ccgtcgtcac tttcggccaa   360
gggacacgac tggagattaa a                                             381

<210> SEQ ID NO 49
<211> LENGTH: 381
<212> TYPE: DNA
<213> ORGANISM: artificial sequence
<220> FEATURE:
<223> OTHER INFORMATION: Variable light chain for the mAb 40C01-Vk3

<400> SEQUENCE: 49
atggagaccg acaccctgct gctgtgggtg ctgctgctgt gggtgcccgg gtcgaccggt    60
gacatccaga tgacccagtc cccaagctcc ctgtctgcct ctgtaggaga cagagtcacc   120
atcacttgcc gggcgagtca gggcgttgac gcttatgttg cctggtatca gcagaaaccg   180
ggaaaagtcc ctaaactcct gatctacagt acatccactt tggcatcagg ggtcccatct   240
cgcttcagtg gtagtggatc tgggacggac ttcactctca ccatcagcag cctgcagcct   300
gaagatgtgg ccacttacta ctgtcaaagt cataacgctg ccgtcgtcac tttcggccaa   360
gggacacgac tggagattaa a                                             381

<210> SEQ ID NO 50
<211> LENGTH: 381
<212> TYPE: DNA
<213> ORGANISM: artificial sequence
<220> FEATURE:
<223> OTHER INFORMATION: Variable light chain for the mAb 40C01-Vk3
    (codon optimized sequence)

<400> SEQUENCE: 50
atggaaaccg acaccctgct cctctgggtg ctgctgctgt gggtgcccgg ctctaccggc    60
gacatccaga tgacccagtc ccctccagc ctgtccgcct ccgtgggcga cagagtgacc   120
atcacctgtc gggcctctca gggcgtggac gcctacgtgg cctggtatca gcagaaaccc   180
ggcaaggtgc ccaagctgct gatctactcc acctccaccc tggcctccgg cgtgccctcc   240
agattctccg gctctggctc cggcaccgac ttcaccctga ccatctccag cctgcagccc   300
gaggacgtgg ccacctacta ctgccagtcc cacaacgccg ccgtggtgac attcggccag   360
ggcacccggc tggaaatcaa g                                             381

<210> SEQ ID NO 51
<211> LENGTH: 113
<212> TYPE: PRT
<213> ORGANISM: artificial sequence
<220> FEATURE:
<223> OTHER INFORMATION: Variable heavy chain for the mAb optimized
    42F03

<400> SEQUENCE: 51

Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Arg Tyr
                20                  25                  30

Arg Met Val Trp Val Arg Gln Ala Pro Gly Lys Gly Leu Glu Trp Val
            35                  40                  45

Ser Trp Ile Ser Pro Ser Gly Gly Ala Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Arg Trp Gly Gln Gly Thr Leu Val Thr Val Ser
            100                 105                 110

Ser

<210> SEQ ID NO 52
<211> LENGTH: 106
<212> TYPE: PRT
<213> ORGANISM: artificial sequence
<220> FEATURE:
<223> OTHER INFORMATION: Variable light chain for the mAb optimized
      42F03

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Gly Ser Ser Ile Thr
                85                  90                  95

Phe Gly Gly Gly Thr Lys Val Glu Ile Lys
            100                 105

<210> SEQ ID NO 53
<211> LENGTH: 126
<212> TYPE: PRT
<213> ORGANISM: artificial sequence
<220> FEATURE:
<223> OTHER INFORMATION: Variable heavy chain for the mAb 80A10

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
                20                  25                  30

Val Met Lys Trp Val Arg Gln Ala Pro Gly Lys Gly Leu Glu Trp Val
            35                  40                  45

Ser Gly Ile Arg Ser Ser Gly Gly Asp Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Arg Gln Ser Arg Tyr Cys Asn Gly Gly Ser Cys Tyr Ser Arg Ala
            100                 105                 110

Phe Asp Ile Trp Gly Gln Gly Thr Met Val Thr Val Ser Ser
            115                 120                 125

<210> SEQ ID NO 54
<211> LENGTH: 107
<212> TYPE: PRT
<213> ORGANISM: artificial sequence
<220> FEATURE:
<223> OTHER INFORMATION: Variable light chain for the mAb 80A10

<400> SEQUENCE: 54

Gln Pro Pro Ser Ala Ser Gly Thr Pro Gly Gln Arg Val Thr Ile Ser
1               5                   10                  15

Cys Phe Gly Ser Asn Ser Asn Ile Gly Ser Thr Tyr Ala Tyr Trp Tyr
            20                  25                  30

Gln Gln Val Pro Gly Thr Ala Pro Lys Leu Leu Ile Tyr Arg Asn Asn
        35                  40                  45

Gln Arg Pro Ser Gly Val Pro Asp Arg Phe Ser Gly Ser Lys Ser Gly
    50                  55                  60

Thr Ser Ala Ser Leu Ala Ile Ser Gly Leu Arg Ser Glu Asp Glu Ala
65                  70                  75                  80

Asp Tyr Tyr Cys Ala Ala Trp Asp Val Asn Leu Ser Gly His Trp Val
                85                  90                  95

Phe Gly Gly Gly Thr Lys Leu Thr Val Leu Gly
            100                 105

<210> SEQ ID NO 55
<211> LENGTH: 120
<212> TYPE: PRT
<213> ORGANISM: artificial sequence
<220> FEATURE:
<223> OTHER INFORMATION: Variable heavy chain for the mAb 80A11

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Pro Met Gly Trp Val Arg Gln Ala Pro Gly Lys Gly Leu Glu Trp Val
        35                  40                  45

Ser Ser Ile Ser Pro Ser Gly Gly Met Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Lys Phe Thr Ser Gly Arg Thr Phe Asp Ile Trp Gly Gln
            100                 105                 110

Gly Thr Met Val Thr Val Ser Ser
        115                 120

<210> SEQ ID NO 56
<211> LENGTH: 108
<212> TYPE: PRT
<213> ORGANISM: artificial sequence
<220> FEATURE:
<223> OTHER INFORMATION: Variable light chain for the mAb 80A11

<400> SEQUENCE: 56

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Val Pro Gly Val Pro Asp Arg Phe Thr Gly
    50                  55                  60

Ser Gly Ser Glu Thr Asp Phe Thr Leu Thr Ile Thr Arg Leu Glu Pro
65                  70                  75                  80

Glu Asp Phe Ala Val Tyr Tyr Cys Gln Leu Ser Ser Ser Pro Ser
                85                  90                  95

Trp Thr Phe Gly Gln Gly Thr Arg Leu Glu Ile Lys
                100                 105

<210> SEQ ID NO 57
<211> LENGTH: 118
<212> TYPE: PRT
<213> ORGANISM: artificial sequence
<220> FEATURE:
<223> OTHER INFORMATION: Variable heavy chain for the mAb 80B09

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asn Met Leu Trp Val Arg Gln Ala Pro Gly Lys Gly Leu Glu Trp Val
        35                  40                  45

Ser Val Ile Ser Pro Ser Gly Gly Arg Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Thr Ser Ile Thr Met Phe Asp Tyr Trp Gly Gln Gly Thr
                100                 105                 110

Leu Val Thr Val Ser Ser
        115

<210> SEQ ID NO 58
<211> LENGTH: 110
<212> TYPE: PRT
<213> ORGANISM: artificial sequence
<220> FEATURE:
<223> OTHER INFORMATION: Variable light chain for the mAb 80B09

<400> SEQUENCE: 58

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ser Tyr
            20                  25                  30

Asn Tyr Val Ser Trp Tyr Gln Gln His Pro Gly Arg Ala Pro Lys Val
        35                  40                  45

Met Ile Tyr Asp Val Thr Tyr Arg Pro Ser Gly Val Ser Asn Arg Phe
    50                  55                  60

```
Ser Gly Ser Lys Ser Gly Asn Thr Ala Ser Leu Thr Ile Ser Gly Leu
 65                 70                  75                  80

Gln Ala Glu Asp Glu Ala Asp Tyr Tyr Cys Gly Ser Tyr Arg Lys Ser
                 85                  90                  95

Ser Leu Tyr Val Phe Gly Thr Gly Thr Lys Val Thr Val Leu
            100                 105                 110

<210> SEQ ID NO 59
<211> LENGTH: 115
<212> TYPE: PRT
<213> ORGANISM: artificial sequence
<220> FEATURE:
<223> OTHER INFORMATION: Variable heavy chain for the mAb 80D11

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Trp Met Gln Trp Val Arg Gln Ala Pro Gly Lys Gly Leu Glu Trp Val
        35                  40                  45

Ser Ser Ile Ser Ser Gly Gly Lys Thr Arg Tyr Ala Asp Ser Val
 50                 55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Thr Ala Gly Tyr Ser Ser Gly Trp Gly Gln Gly Thr Leu Val Thr
            100                 105                 110

Val Ser Ser
        115

<210> SEQ ID NO 60
<211> LENGTH: 110
<212> TYPE: PRT
<213> ORGANISM: artificial sequence
<220> FEATURE:
<223> OTHER INFORMATION: Variable light chain for the mAb 80D11

<400> SEQUENCE: 60

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Leu Ser Trp Tyr Gln Gln His Pro Gly Lys Ala Pro Lys Leu
        35                  40                  45

Met Ile Tyr Gly Val Ser Asn Arg Pro Ser Gly Val Ser Thr Arg Phe
 50                 55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Tyr Cys Ser Ser Tyr Thr Ser Thr
                85                  90                  95

Gly Thr Arg Val Phe Gly Gly Gly Thr Arg Leu Thr Val Leu
            100                 105                 110

<210> SEQ ID NO 61
<211> LENGTH: 113
<212> TYPE: PRT
```

<213> ORGANISM: artificial sequence
<220> FEATURE:
<223> OTHER INFORMATION: Variable heavy chain for the mAb 42F03

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Thr Trp Val Arg Gln Ala Pro Gly Lys Gly Leu Glu Trp Val
        35                  40                  45

Ser Tyr Ile Arg Ser Ser Gly Gly Phe Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Arg Trp Gly Gln Gly Thr Leu Val Thr Val Ser
            100                 105                 110

Ser

<210> SEQ ID NO 62
<211> LENGTH: 107
<212> TYPE: PRT
<213> ORGANISM: artificial sequence
<220> FEATURE:
<223> OTHER INFORMATION: Variable light chain for the mAb 42F03

<400> SEQUENCE: 62

Ile Gln Met Thr Gln Ser Pro Gly Thr Leu Ser Leu Ser Pro Gly Glu
1               5                   10                  15

Arg Ala Thr Leu Ser Cys Arg Ala Ser Gln Ser Val Ser Asn Asn Tyr
            20                  25                  30

Leu Ala Trp Tyr Gln Gln Lys Pro Gly Gln Ala Pro Arg Leu Leu Ile
        35                  40                  45

Ser Gly Ala Ser Arg Arg Ala Thr Asp Ile Ala Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Phe Pro Leu
                85                  90                  95

Thr Phe Gly Gly Gly Thr Lys Val Glu Ile Lys
            100                 105

<210> SEQ ID NO 63
<211> LENGTH: 106
<212> TYPE: PRT
<213> ORGANISM: artificial sequence
<220> FEATURE:
<223> OTHER INFORMATION: Light chain constant region, Lambda constant
      gene 3

<400> SEQUENCE: 63

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 64
<211> LENGTH: 107
<212> TYPE: PRT
<213> ORGANISM: artificial sequence
<220> FEATURE:
<223> OTHER INFORMATION: Light chain constant region, Kappa unique
      constant gene

<400> SEQUENCE: 64

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 65
<211> LENGTH: 107
<212> TYPE: PRT
<213> ORGANISM: artificial sequence
<220> FEATURE:
<223> OTHER INFORMATION: Variable light chain for the mAb 12A01

<400> SEQUENCE: 65

Asp Ile Gln Met Thr Gln Ser Pro Asp Ser Leu Ser Ala Ser Val Gly
 1               5                  10                  15

Asp Arg Val Thr Ile Thr Cys Arg Ala Ser Gln Gly Val Asp Ile Tyr
            20                  25                  30

Val Ala Trp Tyr Gln Gln Lys Pro Gly Lys Val Pro Lys Leu Leu Met
        35                  40                  45

His Ser Ala Ser Thr Leu Ala Ser Gly Val Pro Ser Arg Phe Ser Gly
 50                  55                  60

Arg Gly Ser Gly Thr Asp Phe Thr Leu Thr Ile Asn Ser Leu Gln Ala
 65                  70                  75                  80

Glu Asp Val Ala Thr Tyr Tyr Cys Gln Ser His Asn Ser Ala Val Val
                 85                  90                  95

Thr Phe Gly Gln Gly Thr Arg Leu Glu Ile Lys
            100                 105

<210> SEQ ID NO 66
<211> LENGTH: 399

-continued

```
<212> TYPE: DNA
<213> ORGANISM: artificial sequence
<220> FEATURE:
<223> OTHER INFORMATION: Variable heavy chain for the mAb optimized
      42F03

<400> SEQUENCE: 66
atggagaccg acaccctgct gctgtgggtg ctgctgctgt gggtgcccgg gtcgaccggc    60
gaagttcaat tgttagagtc tggtggcggt cttgttcagc ctggtggttc tttacgtctt   120
tcttgcgctg cttccggatt cactttctct cgttaccgta tggtgtgggt cgccaagct    180 cctggtaaag gtttggagtg gtttcttgg atctctcctt ctggtggcgc aactagctat    240
gctgactccg ttaaaggtcg cttcactatc tctagagaca actctaagaa tactctctac   300
ttgcagatga acagcttaag gctgaggac actgcagtct actattgtgc gagaggcctg    360
taccggtggg gccagggaac cctggtcacc gtctcaagc                          399

<210> SEQ ID NO 67
<211> LENGTH: 378
<212> TYPE: DNA
<213> ORGANISM: artificial sequence
<220> FEATURE:
<223> OTHER INFORMATION: Variable light chain for the mAb optimized
      42F03

<400> SEQUENCE: 67
atggagaccg acaccctgct gctgtgggtg ctgctgctgt gggtgcccgg gtcgaccggt    60
gagatcgtga tgacccagtc tccagccacc ctgtctgtgt ctccaggaga aagagccacc   120
ctctcctgca gggccagtca gagtgtgagt acaaacttag cctggtacca gcagaaacct   180
ggccaggctc ccaggctcct catctatggt gcatccagca gggccactgg catcccagcc   240
aggttcagtg gcagtgggtc tgggacagag ttcactctca ccatcagcag cctgcagtct   300
gaagattttg cagtgtatta ctgtcagcag tatggtagct ccatcacttt cggcggaggg   360
accaaggtgg agatcaaa                                                 378

<210> SEQ ID NO 68
<211> LENGTH: 396
<212> TYPE: DNA
<213> ORGANISM: artificial sequence
<220> FEATURE:
<223> OTHER INFORMATION: Variable light chain for the mAb 80A10

<400> SEQUENCE: 68
atggagaccg acaccctgct gctgtgggtg ctgctgctgt gggtgcccgg gtcgaccggt    60
cagagcgaat tgactcagcc accctcagcg tctgggaccc ccgggcagag ggtcaccatc   120
tcttgttttg ggagcaactc caacatcgga agtacttatg catactggta ccagcaggtc   180
ccaggaacgg cccccaaact cctcatctac cggaataatc agcggccctc agggtccct   240 gaccgattct ctggctccaa gtctggcacc tcagcctccc tggccattag tgggctccgg   300
tccgaggatg aggctgatta ttactgtgca gcatgggatg tcaacctgag tggtcattgg   360
gtgttcggcg gagggaccaa gctgaccgtc ctagga                             396

<210> SEQ ID NO 69
<211> LENGTH: 438
<212> TYPE: DNA
<213> ORGANISM: artificial sequence
<220> FEATURE:
<223> OTHER INFORMATION: Variable heavy chain for the mAb 80A10
```

-continued

<400> SEQUENCE: 69

```
atggagaccg acaccctgct gctgtgggtg ctgctgctgt gggtgcccgg gtcgaccggc      60
gaagttcaat tgttagagtc tggtggcggt cttgttcagc ctggtggttc tttacgtctt     120
tcttgcgctg cttccggatt cactttctct atgtacgtta tgaagtgggt cgccaagct     180
cctggtaaag gtttggagtg ggtttctggt atccgttctt ctggtggcga acttcttat     240
gctgactccg ttaaaggtcg cttcactatc tctagagaca actctaagaa tactctctac     300
ttgcagatga acagcttaag gctgaggac acggccgtgt attactgtgc aagacagagc     360
cggtattgta atggtggtag ctgctactcg cgtgcttttg atatctgggg ccaagggaca     420
atggtcaccg tctcaagc                                                    438
```

<210> SEQ ID NO 70
<211> LENGTH: 384
<212> TYPE: DNA
<213> ORGANISM: artificial sequence
<220> FEATURE:
<223> OTHER INFORMATION: Variable light chain for the mAb 80A11

<400> SEQUENCE: 70

```
atggagaccg acaccctgct gctgtgggtg ctgctgctgt gggtgcccgg gtcgaccggt      60
gacatccaga tgacccagtc tccagccacc ctgtctttgt ctccagggga aagagccacc     120
ctctcctgca gggccagtca gagtgttagc agctacttag cctggtacca acagaaacct     180
ggccaggctc ccaggctcct catctatggt gcgtccagca gggtccctgg cgtcccagac     240
aggttcactg gcagtgggtc tgagacagac ttcactctca ccatcaccag actggagcct     300
gaggattttg cagtctatta ctgtcagctg tctagtagct caccgtcgtg gacgttcggc     360
caggggacac gactggagat taaa                                            384
```

<210> SEQ ID NO 71
<211> LENGTH: 420
<212> TYPE: DNA
<213> ORGANISM: artificial sequence
<220> FEATURE:
<223> OTHER INFORMATION: Variable heavy chain for the mAb 80A11

<400> SEQUENCE: 71

```
atggagaccg acaccctgct gctgtgggtg ctgctgctgt gggtgcccgg gtcgaccggc      60
gaagttcaat tgttagagtc tggtggcggt cttgttcagc ctggtggttc tttacgtctt     120
tcttgcgctg cttccggatt cactttctct cgttacccta tgggttgggt tcgccaagct     180
cctggtaaag gtttggagtg ggtttcttct atctctcctt ctggtggcat gactcgttat     240
gctgactccg ttaaaggtcg cttcactatc tctagagaca actctaagaa tactctctac     300
ttgcagatga acagcttaag gctgaggac acggccgtgt attactgtgc gagacttaaa     360
tttacgtcgg gcagaacttt tgatatctgg ggccaaggga caatggtcac cgtctcaagc     420
```

<210> SEQ ID NO 72
<211> LENGTH: 390
<212> TYPE: DNA
<213> ORGANISM: artificial sequence
<220> FEATURE:
<223> OTHER INFORMATION: Variable light chain for the mAb 80B09

<400> SEQUENCE: 72

```
atggagaccg acaccctgct gctgtgggtg ctgctgctgt gggtgcccgg gtcgaccggt      60
cagagcgctt tgactcagcc tgcctccgtg tctgggtctc ctggacagtc gatcaccatc     120
```

| tcctgcactg gaaccagcag tgacattggg agttataatt atgtctcctg gtaccaacaa | 180 |
| caccaggca gagcccccaa agtcatgatt tatgatgtca cttatcggcc ctcagggtt | 240 |
| tctaatcgct ctctctggctc caagtctggc aacacggcct ccctgaccat ctctgggctc | 300 |
| caggctgagg acgaggctga ttattactgc ggctcatata gaaaaagcag cctttatgtc | 360 |
| ttcggaactg ggaccaaggt caccgtccta | 390 |

<210> SEQ ID NO 73
<211> LENGTH: 414
<212> TYPE: DNA
<213> ORGANISM: artificial sequence
<220> FEATURE:
<223> OTHER INFORMATION: Variable heavy chain for the mAb 80B09

<400> SEQUENCE: 73

| atggagaccg acaccctgct gctgtgggtg ctgctgctgt gggtgcccgg gtcgaccggc | 60 |
| gaagttcaat tgttagagtc tggtggcggt cttgttcagc ctggtggttc tttacgtctt | 120 |
| tcttgcgctg cttccggatt cactttctct aagtacaata tgctttgggt tcgccaagct | 180 |
| cctggtaaag gtttggagtg gtttctgtt atctctcctt ctggtggccg tacttcttat | 240 |
| gctgactccg ttaaaggtcg cttcactatc tctagagaca actctaagaa tactctctac | 300 |
| ttgcagatga acagcttaag ggctgaggac acggccgtgt attactgtgc gagacataca | 360 |
| agtattacta tgtttgacta ctggggccag ggaaccctgg tcaccgtctc aagc | 414 |

<210> SEQ ID NO 74
<211> LENGTH: 390
<212> TYPE: DNA
<213> ORGANISM: artificial sequence
<220> FEATURE:
<223> OTHER INFORMATION: Variable light chain for the mAb 80D11

<400> SEQUENCE: 74

| atggagaccg acaccctgct gctgtgggtg ctgctgctgt gggtgcccgg gtcgaccggt | 60 |
| cagagcgctt tgactcagcc tgcctccgtg tctgggtctc ctggacagtc gatcaccatc | 120 |
| tcctgcactg gaaccagcag tgacgttggt ggttataact atctctcctg gtaccaacag | 180 |
| caccaggca aagcccccaa actcatgatt tatggggtca gtaatcggcc ctcaggagtt | 240 |
| tctactcgct ctctctggctc caagtctggc aacacggcct ccctgaccat ctctgggctc | 300 |
| caggctgagg acgaggctga ttattactgc agctcataca caagcaccgg cactcgggtt | 360 |
| ttcggcggag ggaccagact gaccgtccta | 390 |

<210> SEQ ID NO 75
<211> LENGTH: 405
<212> TYPE: DNA
<213> ORGANISM: artificial sequence
<220> FEATURE:
<223> OTHER INFORMATION: Variable heavy chain for the mAb 80D11

<400> SEQUENCE: 75

| atggagaccg acaccctgct gctgtgggtg ctgctgctgt gggtgcccgg gtcgaccggc | 60 |
| gaagttcaat tgttagagtc tggtggcggt cttgttcagc ctggtggttc tttacgtctt | 120 |
| tcttgcgctg cttccggatt cactttctct cattactgga tgcagtgggt tcgccaagct | 180 |
| cctggtaaag gtttggagtg gtttcttct atctcttctt ctggtggcaa gactcgttat | 240 |
| gctgactccg ttaaaggtcg cttcactatc tctagagaca actctaagaa tactctctac | 300 |

```
ttgcagatga acagcttaag ggctgaggac acggccgtgt attactgtgc cacagccggg      360
tatagcagtg gatggggcca gggaaccctg gtcaccgtct caagc                     405
```

<210> SEQ ID NO 76
<211> LENGTH: 384
<212> TYPE: DNA
<213> ORGANISM: artificial sequence
<220> FEATURE:
<223> OTHER INFORMATION: Variable light chain for the mAb 42F03

<400> SEQUENCE: 76

```
atggagaccg acaccctgct gctgtgggtg ctgctgctgt gggtgcccgg gtcgaccggt      60
gacatccaga tgacccagtc tccaggcacc ctgtctttgt ctccagggga aagagccacc    120
ctctcctgca gggccagtca gagtgttagt aataactact tagcctggta ccagcagaaa    180
cctggccagg ctcccaggct cctcatctct ggtgcatccc gcagggccac tgacatcgca    240
gacaggttca gtggcagtgg gtctggcaca gacttcactc tcaccatcag caggctggag    300
cctgaagatt ttgcagtcta ttactgtcag cagtatgaca gttttcctct caccttcggc    360
ggagggacca aggtggagat caaa                                            384
```

<210> SEQ ID NO 77
<211> LENGTH: 399
<212> TYPE: DNA
<213> ORGANISM: artificial sequence
<220> FEATURE:
<223> OTHER INFORMATION: Variable heavy chain for the mAb 42F03

<400> SEQUENCE: 77

```
atggagaccg acaccctgct gctgtgggtg ctgctgctgt gggtgcccgg gtcgaccggc      60
gaagttcaat tgttagagtc tggtggcggt cttgttcagc ctggtggttc tttacgtctt    120
tcttgcgctg cttccggatt cactttctct tggtacccta tgacttgggt tcgccaagct    180
cctggtaaag gtttggagtg gtttctttat atccgttctt ctggtggctt tactaagtat    240
gctgactccg ttaaaggtcg cttcactatc tctagagaca actctaagaa tactctctac    300
ttgcagatga acagcttaag ggctgaggac actgcagtct actattgtgc gagaggcctg    360
taccggtggg gccagggaac cctggtcacc gtctcaagc                            399
```

<210> SEQ ID NO 78
<211> LENGTH: 381
<212> TYPE: DNA
<213> ORGANISM: artificial sequence
<220> FEATURE:
<223> OTHER INFORMATION: Variable light chain for the mAb 12A01

<400> SEQUENCE: 78

```
atggagaccg acaccctgct gctgtgggtg ctgctgctgt gggtgcccgg gtcgaccggt      60
gacatccaga tgacccagtc tccagactcc ctgtctgcct ctgtaggaga cagagtcacc    120
atcacttgcc gggcgagtca gggcgttgac atttatgttg cctggtatca gcagaaaccg    180
ggaaaagttc ctaaactcct gatgcatagt gcatccactt tggcatcagg ggtcccatct    240
cgcttcagtg gtcgtggatc tgggacggac ttcactctca ccatcaacag cctgcaggct    300
gaagatgttg ccacttacta ctgtcaaagt cataacagtg ccgtcgtcac tttcggccaa    360
gggacacgac tggagattaa a                                               381
```

<210> SEQ ID NO 79
<211> LENGTH: 452

<212> TYPE: PRT
<213> ORGANISM: artificial sequence
<220> FEATURE:
<223> OTHER INFORMATION: Heavy chain for the mAb 40C01-VH1-IgG1

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Val Trp Val Arg Gln Ala Pro Gly Lys Gly Leu Glu Trp Val
        35                  40                  45

Ser Gly Ile Ser Pro Ser Gly Val Thr Arg Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Lys Glu Met Thr Thr Ile Ser Tyr Phe Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

```
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
        450

<210> SEQ ID NO 80
<211> LENGTH: 451
<212> TYPE: PRT
<213> ORGANISM: artificial sequence
<220> FEATURE:
<223> OTHER INFORMATION: Heavy chain for the mAb 40C01-VH1-IgG2_DI-NQ-
      HC2h-subtype

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Val Trp Val Arg Gln Ala Pro Gly Lys Gly Leu Glu Trp Val
        35                  40                  45

Ser Gly Ile Ser Pro Ser Gly Gly Val Thr Arg Tyr Ala Ala Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Lys Glu Met Thr Thr Ile Ser Tyr Phe Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
            195                 200                 205

Asp His Lys Pro Ser Asn Thr Lys Val Asp Lys Thr Val Glu Pro Lys
        210                 215                 220

Ser Ser Asp Lys Thr His Thr Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285
```

```
Val His Asn Ala Lys Thr Lys Pro Arg Glu Glu Gln Ala Gln Ser Thr
    290                 295                 300
Phe Arg Val Val Ser Val Leu Thr Val Val His Gln Asp Trp Leu Asn
305                 310                 315                 320
Gly Lys Glu Tyr Lys Cys Lys Val Ser Asn Lys Gly Leu Pro Ala Pro
                325                 330                 335
Ile Glu Lys Thr Ile Ser Lys Thr Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Met Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 81
<211> LENGTH: 214
<212> TYPE: PRT
<213> ORGANISM: artificial sequence
<220> FEATURE:
<223> OTHER INFORMATION: Light chain for the mAb 40C01-Vk3-c-Kappa

<400> SEQUENCE: 81

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Val Asp Ala Tyr
            20                  25                  30
Val Ala Trp Tyr Gln Gln Lys Pro Gly Lys Val Pro Lys Leu Leu Ile
        35                  40                  45
Tyr Ser Thr Ser Thr Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Ser His Asn Ala Ala Val Val
                85                  90                  95
Thr Phe Gly Gln Gly Thr Arg Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
    195                 200                 205

Phe Asn Arg Gly Glu Cys
    210

<210> SEQ ID NO 82
<211> LENGTH: 98
<212> TYPE: PRT
<213> ORGANISM: Artificial sequence
<220> FEATURE:
<223> OTHER INFORMATION: IGHV3-23*01

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 83
<211> LENGTH: 15
<212> TYPE: PRT
<213> ORGANISM: Artificial sequence
<220> FEATURE:
<223> OTHER INFORMATION: IGHJ4*02

<400> SEQUENCE: 83

Tyr Phe Asp Tyr Trp Gly Gln Gly Thr Leu Val Thr Val Ser Ser
1               5                   10                  15

<210> SEQ ID NO 84
<211> LENGTH: 95
<212> TYPE: PRT
<213> ORGANISM: Artificial sequence
<220> FEATURE:
<223> OTHER INFORMATION: IGKV1-27*01

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

```
<210> SEQ ID NO 85
<211> LENGTH: 12
<212> TYPE: PRT
<213> ORGANISM: Artificial sequence
<220> FEATURE:
<223> OTHER INFORMATION: IGKJ5*01

<400> SEQUENCE: 85

Ile Thr Phe Gly Gln Gly Thr Arg Leu Glu Ile Lys
1               5                   10
```

MONOCLONAL ANTIBODY DIRECTED AGAINST CXCR5

CROSS-REFERENCE TO RELATED APPLICATION

This application is the U.S. national stage application of International Patent Application No. PCT/EP2014/058903, filed Apr. 30, 2014.

The Sequence Listing for this application is labeled "Seq-List.txt" which was created on Oct. 13, 2015 and is 76 KB. The entire contents of the sequence listing is incorporated herein by reference in its entirety.

FIELD OF INVENTION

The present invention relates to antibodies with specificity for CXCR5. More particularly, the invention relates to monoclonal antibodies, and more particularly fully human monoclonal antibodies, that bind specifically to and neutralize human CXCR5 with high affinity. The invention also relates to nucleic acids encoding said antibodies, vectors for expression of these nucleic acids, and host cells for producing said antibodies. Further, the invention relates to the use of said antibodies in the diagnosis and/or treatment of autoimmune or inflammatory diseases, as well as cancers.

BACKGROUND OF THE INVENTION

Naïve B cells engage antigen (Ag) on their B cell receptor (BCR), upregulate CCR7 and migrate to the outer T cell zones to elicit T cell help, leading to differentiation in a T cell dependent or independent manner. T cell independent activation of B cells leads to short-lived IgM antibody secreting plasma cells. However cognate interactions with activated T cells can further augment B cell function and drive follicular differentiation. Congregating T helper cells trafficking through the T cell zones are exposed to the same antigen on MHC class II (MHCII) complexes on antigen presenting cells (APC) such as dendritic cells. Presentation of the antigen-MHCII complex can lead to activation and proliferation of T cells with the relevant antigen receptor. Activated T cells migrate to the B cell areas and engage MHCII-bound Ag on B cells with the same specificity, leading to the formation of an immune synapse. B cells activated in this manner seed the follicles and undergo intense proliferation, differentiating into high-affinity memory B cells or long-lived plasma cells. The criteria for generating high affinity antigen binding B cells through somatic hypermutation of the BCR is controlled by specialist mesenchymal and T cell populations. High affinity antigen binding B cells able to engage and process antigen presented on follicular dendritic cells (FDCs) are selected for further differentiation by interactions with Follicular B Helper T (TFH) cells. Interactions with TFH cells promote the selection of high affinity binders, as well as signalling for differentiation into plasma and long-lived plasma cells. The expression of CXCR5 on B and TFH cells is known to play a key role in optimising these interactions within germinal centres. Specialised microenvironments that foster these T and B cell interactions are created by FDCs that constitutively express CXCL13, which promotes localization and retention of specialized lymphocyte subsets that express CXCR5. In germinal centres, interactions with CXCR5 positive TFH cells are required for the induction of high affinity antibody responses. There is accumulating evidence in the literature that B cells play a role in the pathogenesis of multiple sclerosis (MS) through the production of specific (auto) antibodies that cause myelin destruction. In addition, B cells are involved in all stages of the MS disease process from initiation (antigen capture) to inflammation and tissue damage and could play further roles in MS including, though not limited to, antigen presentation and production of cytokines. In existing MS therapies, B cells have not been directly targeted until recently, with the pilot study using the monoclonal antibody (mAb) rituximab (anti-CD20). However, as many of the current (interferon beta, glucocorticoids, mitoxantrone, natalizumab, fingolimod) and upcoming (alemtuzumab) therapies for MS have the potential to affect B cell behaviour, it is possible that the effects on B cells may contribute to their therapeutic efficacy.

CXCR5 (also known as Burkitt Lymphoma Receptor, i.e. BLR-1, and CD185) is a G-protein coupled seven-transmembrane domain receptors (GPCR 7TM receptor) which is highly expressed on B cells and subpopulations of CD4 T cells. The only known ligand for CXCR5 is the CXC chemokine CXCL13 (also known as BLC or BCA-1). Targeted deletion of CXCR5 indicated that this receptor is involved in B cell migration and localization of B cells in lymph nodes. In the absence of CXCR5, B cells fail to migrate from the T cell rich zones into B cell follicles of spleen with the result that no functional germinal centres are formed. CXCL13 and CXCR5 knockout mice have a similar phenotype, yet interestingly are still capable of mounting a significant antigen specific response albeit much lower than in wild type mice.

CXCL13 is highly expressed in inflamed Central Nervous System (CNS) but is virtually undetectable in normal CNS. Intrathecal production of CXCL13 is thought to be responsible for the recruitment of CXCR5 positive B and T cells into the cerebrospinal fluid (CSF), and the vast majority of B cells in the CSF of MS patients are CXCR5 positive. CXCL13 expression has also been detected in FDCs observed in lymphoid follicle-like structures in the cerebral meninges of patients with secondary progressive MS. The pathogenic B cell response perceived in MS may be the direct product of lymphocyte accumulation in ectopic lymphoid structures which have been shown to modulate B cell function. Furthermore, the close proximity of actively demyelinating lesions may play a major contributory role in driving the chronicity of disease, by generating autoantigen that leads to a persistent autoimmune response. CXCL13 and B-cell activating factor (BAFF; a key regulator of B cell survival) are both markedly and persistently upregulated in the CNS of mice with relapsing remitting or chronic relapsing experimental autoimmune encephalomyelitis (EAE), suggesting that B cell function also plays a role in the chronicity of CNS inflammation in animal models. This finding is consistent with the phenotype of the CXCL13 knockout mice, which exhibit a milder form of EAE compared to wild type controls with rapid resolution of inflammatory symptoms and a complete recovery from disease. These studies have shown that CXCL13 and CXCR5 play an important role in B cell migration, differentiation and proliferative responses. B cells in the vasculature are present in relatively low numbers, therefore positioning within specialised lymphoid microenvironments is critical to interacting with other lymphocyte subsets that dictate B cell effector function. Expression of CXCR5 plays a central role in this process, hence CXCR5 antagonism could potentially block MS disease by reducing recruitment of B and T cells into the CNS, by inhibiting B cell maturation into plasma cells or centrocytes and by blocking interactions with TFH cells and auto-antibody production. Perhaps significantly, CXCR5 blockade could disrupt ectopic lymphoid follicle development by attenuating auto-antigen presentation within these sterile lymphoid environments, and promote resolution of the inflammatory process.

The generation of ectopic lymphoid structures, through expression of CXCL13 and interactions with CXCR5 bearing cells has also been identified in other chronic inflammatory diseases such as rheumatoid arthritis (RA) and Sjögren's syndrome and more recently CXCR5 expression has also been shown in a number of pancreatic carcinomas. Thus, antagonism of CXCR5, via the use of antibodies directed to CXCR5, may also be a useful therapeutic approach in these diseases. This is credible in view of the similarity of expression between CXCL13 (the ligand of CXCR5) and BAFF in the CNS of mice with EAE as disclosed above, and because anti-BAFF therapy is well-established for the treatment of inflammatory/autoimmune disorders. Indeed, different anti-BAFF antibodies are on the market or are being developed for the treatment of inflammatory/autoimmune disorders: for instance, belimumab, already approved for systemic lupus erythematosus (SLE), has also been assessed for diseases such as MS, RA and Sjögren's syndrome, and tabalumab is currently in clinical trials for SLE and MS.

As described above, the CXCL13/CXCR5 pathway plays a key role in B cell functions. Burkle et al. (2007) have also shown the involvement of this pathway in cancer, such as in B-cell chronic lymphocytic leukaemia (B-CLL). It was notably shown that CLL patients have significantly higher serum levels of CXCL13 than healthy patients. The authors were also able to show that anti-CXCR5 antibodies inhibit chemotaxis to CXCL13, suggesting that CXCR5 is a novel therapeutic target for patients with CLL.

WO2009032661 describes humanized antibody polypeptides that specifically bind to the extracellular domain of human CXCR5. It also describes methods of treating a patient having a disorder involving CXCR5 positive cells, comprising administering to said patient a CXCR5 antagonist, which binds CXCR5.

Considering the major impact of inflammatory and/or autoimmune diseases, as well as cancers on public health, there is thus a need for novel molecules that could be useful as medicaments notably for treating inflammatory and/or autoimmune diseases, such as multiple sclerosis, rheumatoid arthritis or Sjögren's syndrome, as well as cancers such as pancreatic carcinomas, B-CLL or cancer/lymphomas involving the CXCR5/CXCL13 pathway.

SUMMARY OF THE INVENTION

The present invention provides new monoclonal antibodies that specifically bind to CXCR5, in particular fully human antibodies. These CXCR5 antibodies are not only able to bind but also to neutralize CXCR5. They are thus able notably to bind to CXCR5$^+$ cells, such as B cells.

In the first embodiment, the invention describes antibodies, or portion thereof, binding to CXCR5 via their complementarity determining regions (CDRs) sequences. Antibodies comprising said CDRs retain CXCR5-binding specificity of the parent molecule from which the CDRs were obtained.

In a further embodiment, the framework regions (FRs) of said antibodies are described. Said FRs are to be combined with the CDRs according to the present invention.

In another embodiment, also disclosed are the amino acid sequences of the variable heavy and light chain of the antibodies of interest, as well as the preferred constant regions to which they can be combined.

Yet another embodiment of the present invention consists of the polynucleotide sequences encoding the antibody of the present invention, vectors and cell lines comprising said polynucleotide sequences.

Also described is a method for producing the antibodies according to the present invention.

Another embodiment of the present invention is a pharmaceutical composition comprising one or at least one of the antibodies of interest.

In a last embodiment, the monoclonal antibodies according to the present invention are for use as a medicament. In particular, they can be used for the treatment of disorders associated with CXCR5, or CXCR5 pathway, and as such can be used for the treatment of autoimmune or inflammatory diseases. In particular, such disorders or diseases are selected from multiple sclerosis, rheumatoid arthritis or Sjogren's syndrome. They can also be used for the treatment of cancers, such as pancreatic carcinomas, B-CLL or other types of cancers involving the CXCR5/CXCL13 pathway.

DEFINITIONS

The term "immunoglobulin" (Ig) refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. A light chain has two parts: the variable domain (VL) and the constant domain (CL), which in the context of a light chain can be called constant region as well. A heavy chain has two parts as well: the variable domain (VH) and the constant region (CH). In each pair, the light and heavy chain variable domains are together responsible for binding to an antigen, and the constant regions are responsible for the antibody effector functions. Full-length immunoglobulin "light chains" (usually about 25 kDa) are encoded by a variable domain gene at the N-terminus (usually about 110 amino acids) and a kappa or lambda constant domain ($C_K$ and $C_\lambda$, respectively) gene at the C-terminus. Full-length immunoglobulin "heavy chains" (usually about 50 kDa), are similarly encoded by a variable domain gene (usually about 116 amino acids) and one of the other constant region genes (usually about 330 amino acids) mentioned hereinafter. There are five types of mammalian heavy chain denoted by the Greek letters: [alpha], [delta], [epsilon], [gamma], and [mu]. The type of heavy chain defines the antibody's isotype as IgA, IgD, IgE, IgG and IgM, respectively. The constant region is identical in all antibodies of the same isotype, but differs in antibodies of different isotypes. Heavy chains [gamma], [alpha] and [delta] have a constant region composed of three Ig constant domains (CH1, CH2, and CH3), and a hinge region for added flexibility; heavy chains [mu] and [epsilon] have a constant region composed of four Ig constant domains (CH1, CH2, CH3, and CH4) and a hinge region.

An immunoglobulin light or heavy chain variable domain consists of a "framework" region interrupted by three hypervariable regions. Thus, the term "hypervariable region" refers to the amino acid residues of an antibody which are responsible for antigen binding. The hypervariable region comprises amino acid residues from a "complementarity determining region" or "CDR", i.e. L-CDR1, L-CDR2 and L-CDR3 in the light chain variable domain and H-CDR1, H-CDR2 and H-CDR3 in the heavy chain variable domain (Kabat et al. 1991) and/or those residues from a "hypervariable loop" (Chothia and Lesk, 1987). "Framework region" or "FR" residues are those variable domain residues other than the hypervariable region residues as herein defined. The sequences of the framework regions of different light (i.e. L-FR1, L-FR2, L-FR3 and L-FR4) or heavy (i.e. H-FR1, H-FR2, H-FR3 and H-FR4) chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

The term "antibody", and its plural form "antibodies", as used herein includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). Genetically engineered intact antibodies or fragments, such as chimeric antibodies, scFv and Fab fragments, as well as synthetic antigen-binding peptides and polypeptides, are also included.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor" (humanization by grafting non-human CDRs onto human framework and constant regions, or by incorporating the entire non-human variable domains onto human constant regions (chimerization)). Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and a few residues in the heavy chain constant region if modulation of the effector functions is needed, are substantially identical to corresponding parts of natural human immunoglobulin sequences. A "humanized antibody" is an antibody comprising a humanized light chain variable domain and a humanized heavy chain variable domain. In some instances, humanized antibodies may retain non-human residues within the human framework regions to enhance proper binding characteristics and/or some amino acid mutations may be introduced within the CDRs in order to improve the binding affinity and/or to reduce the immunogenicity and/or to increase the degree of humanness and/or to improve the biochemical/biophysical properties of the antibody. Through humanizing antibodies, biological half-life may be increased, and the potential for adverse immune reactions upon administration to humans is reduced.

The term "fully human" immunoglobulin refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. A "fully human antibody", or "fully human monoclonal antibody", is an antibody comprising a fully human light chain variable domain and a fully human heavy chain variable domain. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

As used herein, the term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv," "single-chain antibodies," "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

The term "treatment" within the context of this invention refers to any beneficial effect on progression of disease, including attenuation, reduction and decrease or diminishing of the pathological development after onset of disease.

The term "pharmaceutically acceptable" is meant to encompass any carrier, which does not interfere with the effectiveness of the biological activity of the active ingredient and that is not toxic to the host to which it is administered. For example, for parenteral administration, the active protein(s) may be formulated in a unit dosage form for injection in vehicles such as, but not limited to, saline, dextrose solution, serum albumin and Ringers solution.

The human immune system has evolved to combat myriad viral, microbial, and other threats. The humoral component—the antibody response—is a critical component of the immune system's arsenal. Antibodies can coat, block, and process the foreign invader and, importantly, recruit immune effector cells to bring a wide array of defenses to bear against the offender. There are multiple antibody classes and isotypes in the human immune system, each endowed with a palette of effector functions, presumably tailored to the nature of the invading pathogen. Recombinant therapeutic antibodies are built from human sequences and are almost always derived from the IgG class. To date, the majority of therapeutic antibodies are derived from the IgG1 isotype, seconded by IgG2 and IgG4. The IgG1 isotype has a wide utility because of its built-in ability to engage immune effector cells and complement. Effector functions mediated by antibodies and effector cells include principally cytolysis (ADCC=antibody-dependent cell-mediated cytotoxicity), phagocytosis (ADCP=antibody-dependent cell mediated phagocytosis), and complement-dependent cytotoxicity (CDC). Much of our understanding of these effector functions comes from in vitro analysis of antibody mediated killing. For example, incubation of human PBMCs (peripheral blood mononuclear cells) with target cells (typically a tumor cell line) and target-specific antibody leads to lysis of the target cells over a period of hours. Most, if not all, of this ADCC is performed by natural killer (NK) cells. It has been determined that the classic IgG effector functions are mediated through appropriately named Fcγ receptors (Nimmerjahn and Ravetch, 2011). In humans, the FcγRs include three activating receptors, FcγRI, FcγRIIa, and FcγRIIIa, and these are expressed to varying levels and exclusivities on leukocytes. All signal through an ITAM intracellular domain, leading to a signaling cascade resulting in the cognate effector functions of each FcγR-expressing cell. NK cells express FcγRIIIa almost exclusively, and this receptor is definitively responsible for mediating in vitro ADCC. The classical (antibody-dependent) complement pathway, triggered by engagement of the antibody Fc with complement protein C1q, includes non cellular and cellular mechanisms, as well as synergy between complement and FcγR pathways.

DETAILED DESCRIPTION OF THE INVENTION

The present invention is based on the discovery of novel monoclonal antibodies, more particularly fully human monoclonal antibodies that are specific to CXCR5. In particular, they are specific to both human and macaque (for instance *Macaca fascicularis*) forms of CXCR5, i.e. they are cross-reactive. These antibodies, as antagonists of CXCR5, can be useful for treating inflammatory and/or autoimmune disorders or diseases, such as multiple sclerosis (MS), rheumatoid arthritis (RA) or Sjögren's syndrome. They can also be used for the treatment of cancers, such as pancreatic carcinomas, B-CLL or other types of cancers involving CXCR5/CXCL13 pathway.

The invention provides the use of monoclonal antibodies that recognize, bind, modulate and/or neutralize CXCR5, preferably both the human and macaque (for instance *Macaca fascicularis*) forms of CXCR5. In particular, the invention provides the use of light and heavy chain variable domains that bind, modulate and/or neutralize CXCR5, preferably both the human and macaque (for instance *Macaca fascicularis*) forms of CXCR5. In addition, the monoclonal antibodies according to the present invention inhibit CXCL13 signalling through CXCR5. It has been shown (see examples section) that they are able to inhibit CXCL13-induced intracellular calcium flux, inhibit CXCL13-induced chemotaxis and CXCL13 induced ERK phosphorylation. They are also capable to mediate ADCC against primary human B cells. The antibodies according to the invention are preferably depleting antibodies, i.e. having the advantage that they can eliminate both autologous T and B cells, as well as associated dendritic cells and macrophages. Their light and heavy chain variable domains can be fused, respectively, to a kappa or lambda constant domain and to a constant region of a heavy chain chosen among any isotype (IgA, IgD, IgE, IgG and IgM), and expressed in a variety of host cells. Preferably, the constant region chosen is that of an IgG, and more preferably of an IgG1, IgG2 or IgG4 and even more preferably of an IgG1. The antibody, or portion thereof, according to the present invention can be either glycosylated/aglycosylated and/or fucosylated/afucosylated. The preferred antibodies according to the invention have a lower fucose content or are afucosylated, allowing an enhanced ADCC.

According to a first embodiment, any one of the monoclonal antibodies according to the invention, or portions thereof, that binds to CXCR5, comprises a heavy chain variable domain comprising H-CDR1, H-CDR2 and H-CDR3, and a light chain variable domain comprising L-CDR1, L-CDR2 and L-CDR3. Preferably, 1) the heavy chain variable domain comprises H-CDR1, H-CDR2 and H-CDR3 wherein H-CDR1 consists of an amino acid sequence selected from the group consisting of SEQ ID NOs: 8 and 9; H-CDR2 consists of an amino acid sequence selected from the group consisting of SEQ ID NOs: 10 and 11, and H-CDR3 consists of an amino acid sequence selected from the group consisting of SEQ ID NOs: 12 and 13 and 2) the light chain variable domain comprising L-CDR1, L-CDR2 and L-CDR3, wherein L-CDR1 consists of an amino acid sequence selected from the group consisting of SEQ ID NOs:14 and 15; L-CDR2 consists of an amino acid sequence selected from the group consisting of SEQ ID NOs: 16 and 17, and L-CDR3 consists of an amino acid sequence selected from the group consisting of SEQ ID NOs: 18 and 19. Even more preferably, the monoclonal antibodies according to the present invention have their set of H-CDR1, H-CDR2 and H-CDR3 comprising or consisting respectively of: 1) amino acid sequences SEQ ID NOs: 8, 10 and 12, 2) amino acid sequences SEQ ID NOs: 8, 11 and 12; or 3) amino acid sequences SEQ ID NOs: 9, 11 and 13. Similarly, the monoclonal antibodies preferably have their set of L-CDR1, L-CDR2 and L-CDR3 comprising or consisting respectively of: 1) amino acid sequences SEQ ID NOs: 14, 16 and 18, 2) amino acid sequences SEQ ID NOs: 15, 17 and 18, or 3) amino acid sequences SEQ ID NOs: 15, 17 and 19.

In another embodiment, the invention provides a monoclonal antibody, or portion thereof, as described herein wherein 1) the heavy chain variable domain of the monoclonal antibodies comprises framework regions (FRs) H-FR1, H-FR2, H-FR3 and H-FR4, wherein: H-FR1 consists of an amino acid sequence of SEQ ID NO: 20, H-FR2 consists of an amino acid sequence selected from the group consisting of SEQ ID NOs: 21 and 22, H-FR3 consists of an amino acid sequence selected from the group consisting of SEQ ID NOs: 23 and 24, and H-FR4 consists of an amino acid sequence of SEQ ID NO: 25; and 2) the light chain variable domain comprises L-FR1, L-FR2, L-FR3 and L-FR4, wherein: L-FR1 consists of an amino acid sequence selected from the group consisting of SEQ ID NOs: 26, 27 and 28, L-FR2 consists of an amino acid sequence selected from the group consisting of SEQ ID NOs: 29, 30 and 31, L-FR3 consists of an amino acid sequence selected from the group consisting of SEQ ID NOs: 32 and 33, and L-FR4 consists of an amino acid sequence consisting of SEQ ID NO: 34. Preferably, the monoclonal antibodies as described herein have their heavy chain variable domain set of H-FR1, H-FR2, H-FR3 and H-FR4 comprising or consisting respectively of 1) amino acid sequences SEQ ID NOs: 20, 21, 23 and 25, or 2) amino acid sequences SEQ ID NOs: 20, 22, 24 and 25, and their light chain variable domain set of L-FR1, L-FR2, L-FR3 and L-FR4 comprising or consists respectively of: 1) amino acid sequences SEQ ID NOs: 26, 29, 32 and 34, or 2) amino acid sequences SEQ ID NOs: 27, 30, 33 and 34, or 3) amino acid sequences SEQ ID NOs: 28, 31, 33 and 34. Preferably, the H-FRs and L-FRs according to the present invention are associated to the H-CDRs and L-CDRs above described.

In yet another embodiment, the invention provides a monoclonal antibody, or a portion thereof, preferably a fully human monoclonal antibody, wherein the heavy chain variable domain comprises or consists of an amino acid sequence selected from the group consisting of SEQ ID NOs: 1, 3, 4, 51, 53, 55, 57, 59 and 61; and the light chain variable domain comprises or consists of an amino acid sequence selected from the group consisting of SEQ ID NOs: 2, 5, 6, 7, 52, 54, 56, 58, 60, 62 and 65. In a preferred embodiment, the invention provides a monoclonal antibody wherein the heavy chain variable domain comprises or consists of an amino acid sequence selected from the group consisting of SEQ ID NOs: 1, 3 and 4; and the light chain variable domain comprises or consists of an amino acid sequence selected from the group consisting of SEQ ID NOs: 2, 5, 6 and 7. Preferably, the combinations variable heavy chain and variable light chain are selected from the group consisting of 1) SEQ ID NOs: 1 and 2 (mAb called 40C01), 2) SEQ ID NOs: 3 and 7 (mAb called 40C01-VH1-Vk3), and 3) SEQ ID NOs: 4 and 7 (mAb called 40C01-VH2-Vk3). A significant increase in thermal stability of the Fab is obtained with a variable heavy chain having an amino acid sequence according to SEQ ID NO: 3 or 4, together with a variable light chain having an amino acid sequence according to SEQ ID NO: 5, 6 or 7; as compared to the parental mAb 40C01 (SEQ ID NOs 1 and 2). Best results are obtained with 40C01-VH1-Vk3 and 40C01-VH2-Vk3. In an alternative embodiment, the combinations variable heavy chain and variable light chain can also be selected from the group consisting of 1) SEQ ID NOs: 51 and 52 (mAb called optimized 42F03), 2) SEQ ID NOs: 53 and 54 (mAb called 80A10), 3) SEQ ID NOs: 55 and 56 (mAb called 80A11), 4) SEQ ID NOs: 57 and 58 (mAb called 80B09), 5) SEQ ID NOs: 59 and 60 (mAb called 80D11), 5) SEQ ID NOs: 61 and 62 (mAb called 42F03), and 6) SEQ ID NOs:1 and 65 (mAb called 12A01).

Additional heavy chain variable region amino acid sequences having at least 90% or more, at least 95% or more, or at least 99% or more sequence identity to the heavy chain variable region sequences disclosed herein are also provided. Additional light chain variable region amino acid sequences having at least 90% or more, at least 95% or more, or at least 99% or more sequence identity to the light chain variable region sequences disclosed herein are also provided.

The engineered monoclonal antibodies, preferably fully human antibodies, according to the present invention, may comprise any type of heavy chain constant domains, or portion thereof, from any class of antibody, including IgM, IgG, IgD, IgA and IgE, and any subclass (isotype), including notably IgG1, IgG2, IgG3 and IgG4. When it is desired that the antibody exhibits cytotoxic activity, the heavy chain constant domain is usually a complement-fixing constant domain and the class is typically of IgG1 class. When such cytotoxic activity is not desirable, the constant domain may be of the IgG2 or IgG4 class. The engineered antibody may comprise sequences from more than one class or isotype.

In the context of the present invention, IgG1, IgG2 or IgG4 classes of IgG can be used. For instance, the following sequences for the heavy chain constant regions can be used: 1) an IgG1 of allotype G1m(f) having arginine at position 214 in CH1 domain and glutamic acid and methionine at position 356 and 358, respectively, as indicated in the EU index proposed by Kabat et al. of human IgG, (Press and Hogg, Biochem J. 1970) and as disclosed in SEQ ID NO:38, 2) an IgG2 isotype (subtype HC2h, as described in WO2009010290) having a sequence as disclosed in SEQ ID NO:39, or 3) IgG4 isotype as described in Angal et al., 1993 in which serine at position 228 and arginine at position 409 indicated in the EU index proposed by Kabat et al. of human IgG4 are substituted with proline and lysine, respectively, having a sequence as disclosed in SEQ ID NO:40. It is to be understood that the above mentioned constant region sequences can be used in full or only part thereof, such as CH1, CH2 and/or CH3 portion thereof. Non-limiting examples of heavy chains containing both a variable domain and a constant domain are the amino acid sequences disclosed in SEQ ID NOs: 79 and 80. The engineered monoclonal antibodies according to the present invention may also comprise any type of light chain immunoglobulin constant genes, i.e. kappa unique constant gene or lambda constant genes 1, 2, 3, 6 or 7. For instance, the following sequences for the light chain constant regions can be used: a lambda constant gene 3, such as the one described in SEQ ID NO: 63, or the kappa unique constant gene, such as the one described in SEQ ID NO: 64. Non-limiting example of light chain containing both a variable domain and a constant domain is the amino acid sequence disclosed in SEQ ID NO: 81.

A further embodiment of the present invention is an isolated nucleic acid molecule, or a polynucleotide, encoding any of the antibodies or portions thereof herein described, or a complementary strand or degenerate sequence thereof. In this regard, the terms "nucleic acid molecule", or interchangeably "polynucleotide" encompass all different types of nucleic acids, including without limitation deoxyribonucleic acids (e.g., DNA, cDNA, gDNA, synthetic DNA, etc.), ribonucleic acids (e.g., RNA) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

In another embodiment a nucleic acid molecule, also called polynucleotide, encodes the heavy chain of any one of the monoclonal antibodies of the invention, or portions thereof, such as the heavy chain variable domain, and another polynucleotide encodes the light chain of any one of the antibodies of the invention, or portions thereof, such as the light chain variable domain. In an alternative embodiment a unique polynucleotide encodes both the heavy and light chain of any one of the antibodies of the invention, or portions thereof, such as the variable domains or Fab regions.

In a preferred embodiment, the polynucleotide encoding the heavy chain variable domain of an antibody of the invention comprises or consists of SEQ ID NO: 41, 43, 44, 45, 46, 66, 69, 71, 73, 75 or 77. In a preferred embodiment the polynucleotide encoding the light chain variable domain of an antibody of the invention comprises or consists of SEQ ID NO: 42, 47, 48, 49, 50, 67, 68, 70, 72, 74, 76 or 78. In an alternative embodiment a unique polynucleotide encodes both the heavy and light chain variable domains of any one of the antibodies of the invention, wherein the polynucleotide encoding the heavy chain variable domain comprises or consists of SEQ ID NO: 41, 43, 44, 45, 46, 66, 69, 71, 73, 75 or 77 and the polynucleotide encoding the light chain variable domain comprises or consists of SEQ ID NO: 42, 47, 48, 49, 50, 67, 68, 70, 72, 74, 76 or 78. The 57 first nucleotides of SEQ ID NOs: 43 to 46, the 60 first nucleotides of SEQ ID NOs: 41-42, 47-50, 66-70, 69-75 or 77-78, as well as the 63 first nucleotides of SEQ ID NO: 76 or the 75 first nucleotides of SEQ ID NO: 68 encode the leader sequence. In the context of the invention, it is to be understood that these nucleotides can be removed or replaced by any other nucleotide sequences encoding a leader sequence. Therefore, in another embodiment, the polynucleotide encoding the heavy chain variable domain of an antibody of the invention comprises or consists of nucleotides 61 to 429 of SEQ ID NO:41, nucleotides 58 to 426 of SEQ ID NO:43, nucleotides 58 to 426 of SEQ ID NO:44, nucleotides 58 to 426 of SEQ ID NO:45, nucleotides 58 to 426 of SEQ ID NO:46, nucleotides 61 to 399 of SEQ ID NO:66, nucleotides 61 to 438 of SEQ ID NO:69, nucleotides 61 to 420 of SEQ ID NO:71, nucleotides 61 to 414 of SEQ ID NO:73, nucleotides 61 to 405 of SEQ ID NO:75 or nucleotides 61 to 399 of SEQ ID NO:77. Similarly, in a preferred embodiment, the polynucleotide encoding the light chain variable domain of an antibody of the invention comprises or consists of nucleotides 61 to 381 of SEQ ID NO: 42, nucleotides 61 to 381 of SEQ ID NO:47, nucleotides 61 to 381 of SEQ ID NO:48, nucleotides 61 to 381 of SEQ ID NO:49, nucleotides 61 to 381 of SEQ ID NO:50, nucleotides 61 to 378 of SEQ ID NO:67, nucleotides 76 to 396 of SEQ ID NO:68, nucleotides 61 to 384 of SEQ ID NO:70, nucleotides 61 to 390 of SEQ ID NO:72, nucleotides 61 to 390 of SEQ ID NO:74, nucleotides 64 to 384 of SEQ ID NO:76 or nucleotides 61 to 381 of SEQ ID NO:78. In an alternative embodiment a unique polynucleotide encodes both the heavy and light chain variable domains of any one of the antibodies of the invention, wherein the polynucleotide encoding the heavy chain variable domain comprises or consists of nucleotides 61 to 429 of SEQ ID NO:41, nucleotides 58 to 426 of SEQ ID NO:43, nucleotides 58 to 426 of SEQ ID NO:44, nucleotides 58 to 426 of SEQ ID NO:45, nucleotides 58 to 426 of SEQ ID NO:46, nucleotides 61 to 399 of SEQ ID NO:66, nucleotides 61 to 438 of SEQ ID NO:69, nucleotides 61 to 420 of SEQ ID NO:71, nucleotides 61 to 414 of SEQ ID NO:73, nucleotides 61 to 405 of SEQ ID NO:75 or nucleotides 61 to 399 of SEQ ID NO:77 and the polynucleotide encoding the light chain variable domain comprises or consists of 61 to 381 of SEQ ID NO: 42, nucleotides 61 to 381 of SEQ ID NO:47, nucleotides 61 to 381 of SEQ ID NO:48, nucleotides 61 to 381 of SEQ ID NO:49, nucleotides 61 to 381 of SEQ ID NO:50, nucleotides 61 to 378 of SEQ ID NO:67, nucleotides 76 to 396 of SEQ ID NO:68, nucleotides 61 to 384 of SEQ ID NO:70, nucleotides 61 to 390 of SEQ ID NO:72, nucleotides 61 to 390 of SEQ ID NO:74, nucleotides 64 to 384 of SEQ ID NO:76 or nucleotides 61 to 381 of SEQ ID NO:78.

Due to the degeneracy of the genetic code, it is to be understood that the polynucleotides encoding the antibodies according to the present invention can be optimized. Therefore, polynucleotide sequences having at least 90% or more, at least 95% or more, or at least 99% or more sequence identity to the polynucleotide sequences encoding the heavy chain variable region sequences disclosed herein, such as the preferred polynucleotide sequences listed above, are also provided. Similarly, polynucleotide sequences having at least 90% or more, at least 95% or more, or at least 99% or more sequence identity to the polynucleotide sequences encoding the light chain variable region sequences disclosed herein, such as the preferred polynucleotide sequences listed above, are also provided.

A further embodiment of this invention is a vector comprising DNA encoding any of the antibodies described herein or portions thereof, such as the variable domains (heavy and/or light variable domains) or Fab regions. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise the entire or part of the coding sequences for both the heavy and light chain, or either of the light and heavy chain coding sequences, or any portions thereof. Should the vector comprise coding sequences for both heavy and light chains, and portions thereof, these coding sequences may each be operably linked to a promoter. The promoter may be the same or different for the heavy and light chain coding sequences, or portions thereof. The heavy and light chain coding sequences, or portions thereof, may also be operably linked to one single promoter, in this case the coding sequences for the heavy and light chains, or portions thereof, may preferably be separated by an internal ribosomal entry site (IRES). Suitable promoters for eukaryotic gene expression are, for example, promoters derived from viral genes such as the murine or human cytomegalovirus (CMV), the mouse bi-directional CMV promoter, the rous sarcoma virus (RSV) promoter or the human elongation factor-1 alpha (EF-1α) promoter, which are well known to the person skilled in the art. The vector may comprise regulatory elements, such as a promoter, terminator, enhancer, selection marker, origin of replication, insulator etc. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

A further embodiment of the present invention is a recombinant host cell, wherein said cell comprises one or more nucleic acid molecule(s)/polynucleotide(s) or one or more vector(s) as defined above. The host cell may be a prokaryotic or eukaryotic cell. Examples of prokaryotic cells include bacteria, such as E. coli. Examples of eukaryotic cells are yeast cells, plant cells, mammalian cells and insect cells including any primary cell culture or established cell line (e.g., 3T3, Vero, HEK293, TN5, etc.). Suitable host cells for the expression of glycosylated proteins are derived from multicellular organisms. Examples of preferred useful mammalian host cell lines include CHO, HEK293, NS0, SP2/0 and COS cells. The antibodies of the present invention may be produced by any technique known in the art, such as by recombinant technologies, chemical synthesis, cloning, ligations, or combinations thereof. Should it be necessary to obtain an antibody having a lower glycosylation level, an aglycosylated antibody or aglycosylated part thereof, such as an aglycosylated Fc portion, a yeast expression system or engineered/glycoengineered, CHO cell lines can be advantageously used. Similarly, should it be necessary to obtain an antibody having a lower fucosylation level, an afucosylated antibody or afucosylated part thereof, such as an afucosylated Fc portion, a engineered/glycoengineered yeast expression system or engineered/glycoengineered CHO cell lines can be advantageously used.

Another embodiment of this invention is therefore a method of producing an antibody of the present invention, or portions thereof, such as the variable domains (heavy and/or light variable domains) or Fab regions, the method comprising culturing a recombinant host cell of the invention under conditions allowing expression of the nucleic acid molecule(s) encoding any of the antibodies described herein or portions thereof, and recovering/isolating the polypeptide(s) produced. The polypeptide(s) produced may be glycosylated or not, may be fucosylated or not or may contain other post-translational modifications depending on the host cell type used. The method of producing an antibody of the present invention, or portions thereof, may further comprise the steps of purifying the antibodies, or portions thereof, and/or formulating said antibodies, or portions thereof, into a pharmaceutical composition.

Other methods for preparing the polynucleotides (including DNA and RNA) encoding the antibodies described herein, including portions thereof, such as the variable domains (heavy and/or light variable domains) or Fab regions are well known in the art. Total RNA can be prepared using guanidinium isothiocyanate extraction followed by isolation by centrifugation in a CsCl gradient (Chirgwin J M et al. 1979). Poly(A)+ RNA is prepared from total RNA using the method of Aviv and Leder (Aviv H et al. 1972). Complementary DNA (cDNA) is prepared from poly(A)+RNA using known methods. Alternatively, genomic DNA can be isolated. Polynucleotides encoding CXCR5 antibodies, or portions thereof, are then identified and isolated by, for example, hybridization or PCR. The antibodies disclosed herein, including portions thereof, such as the variable domains (heavy and/or light variable domains) or Fab regions, may be produced by any technique known in the art, such as recombinant technologies, chemical synthesis, cloning, ligations, or combinations thereof. Many books and reviews provide teachings on how to clone and produce recombinant proteins using vectors and prokaryotic or eukaryotic host cells.

A further embodiment of the present invention is a pharmaceutical composition comprising the monoclonal antibody according to the invention, or portions thereof, such as the variable domains (heavy and/or light variable domains) or Fab regions. Preferably, said pharmaceutical composition may further comprise at least one additional excipient, such as buffer, stabilizer, surfactant, carriers, diluents, vehicles, etc.

Pharmaceutical compositions according to the invention are useful in the diagnosis, prevention, and/or treatment (local or systemic) of inflammatory or autoimmune diseases/disorders, such as multiple sclerosis, rheumatoid arthritis or Sjogren's syndrome, as well as various types of cancers such as pancreatic carcinomas, B-CLL or other forms of cancer involving CXCR5/CXCL13 pathway. The pharmaceutical compositions of the invention may be administered with a pharmaceutically acceptable carrier.

In another aspect, the invention provides the monoclonal antibodies according to the invention, or portions thereof, such as the variable domains (heavy and/or light variable domains) or Fab regions, for use as a medicament. In particular, they are to be used for the treatment of an inflammatory or an autoimmune disease/disorder. Preferably, said disorder/disease is selected from MS, RA or Sjögren's syndrome. In another aspect, the invention provides a method of treating a disease in a patient, comprising administering to the patient a pharmaceutical composition or any one of the antibodies, or portions thereof, according to the invention. Preferably, the disease is an inflammatory or an autoimmune disease/disorder, such as MS, RA or Sjögren's syndrome. In a further aspect, the invention relates to method of treating cancers, comprising administering to the patient a pharmaceutical composition or any one of the antibodies, or portions thereof, according to the invention. Preferably the cancer is pancreatic carcinomas, B-CLL or any types of cancers involving the CXCR5/CXCL13 pathway.

In another aspect, the invention provides for the use of monoclonal antibody according to the invention for the preparation of a medicament for the treatment of an inflammatory or an autoimmune disease/disorder, as well as a cancer. Preferably, said inflammatory or autoimmune disorder/disease is selected from MS, RA or Sjögren's syndrome. Preferably said cancer is pancreatic carcinomas, B-CLL or any types of cancer involving the CXCR5/CXCL13 pathway. The pharmaceutical composition according to the invention can be administered in any suitable way, such as intravenously, intramuscularly, subcutaneously or intradermally.

For parenteral (e.g. intravenous, subcutaneous, intramuscular, intradermal) administration, a pharmaceutical composition of the invention can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques. The dosage administered to an individual will vary depending upon a variety of factors, including pharmacokinetic properties, the route of administration, patient conditions and characteristics (notably sex, age, body weight, health, and size), extent of symptoms, concurrent treatments, frequency of treatment and the effect desired. The antibodies of the present invention, or portions thereof, such as the variable domains (heavy and/or light variable domains) or Fab regions, can be produced, formulated, administered or used in other alternative forms that can be preferred according to the desired method of use and/or production. Useful conjugates or complexes can also be generated for improving the agents in terms of drug delivery efficacy. For this purpose, the antibodies described herein can be in the form of active conjugates or complex with molecules such as polyethylene glycol and other natural or synthetic polymers (Harris J M et al. 2003). In this regard, the present invention contemplates chemically modified antibodies, in which the antibody is linked with a polymer. Typically, the polymer is water soluble so that the conjugate does not precipitate in an aqueous environment, such as a physiological environment. Moreover, a mixture of polymers can be used to produce the conjugates. The conjugates used for therapy can comprise pharmaceutically acceptable water-soluble polymer moieties. Suitable water-soluble polymers include polyethylene glycol (PEG), monomethoxy-PEG, aryloxy-PEG, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers. Examples of conjugates comprise any of the antibodies disclosed here above and a polyalkyl oxide moiety attached to the N-terminus. PEG is one suitable polyalkyl oxide. As an illustration, any of the antibodies disclosed herein can be modified with PEG, a process known as "PEGylation". PEGylation can be carried out by any of the PEGylation reactions known in the art (Francis G E et al. 1998). For example, PEGylation can be performed by an acylation reaction or by an alkylation reaction with a reactive polyethylene glycol molecule. Preferably, none of these modifications affect significantly the ability of the antibody to bind human or macaque (such as *Macaca fascicularis*) CXCR5.

The present invention also includes recombinant antibodies, or portions thereof, such as the variable domains (heavy and/or light variable domains) or Fab regions, against human and/or macaque (such as *Macaca fascicularis*) CXCR5 that are functionally equivalent to those described above. Modified antibodies, or portions thereof, providing improved stability and/or therapeutic efficacy are also included. Examples of modified antibodies, or portions thereof, include those with conservative substitutions of amino acid residues, and one or more deletions or additions of amino acids which do not significantly deleteriously alter the antigen binding utility. Substitutions can range from changing or modifying one or more amino acid residues to complete redesign of a region, as long as the therapeutic utility is maintained. Antibodies of the present invention, or portions thereof, can be modified post-translationally (e.g., acetylation, oxidation, deamidation, racemization and phosphorylation) or can be modified synthetically (e.g., the attachment of a labelling group). It is understood that the antibodies, or portions thereof, designed by the present method may have additional conservative amino acid substitutions which have substantially no effect on antigen binding or other immunoglobulin functions.

The monoclonal antibodies of the present invention, or portions thereof, such as the variable domains (heavy and/or light variable domains) or Fab regions, can include derivatives. For example, but not by way of limitation, the derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Additionally, the derivative may contain one or more non-classical and/or non-natural amino acids. The in vivo half-lives of the monoclonal antibodies of the present invention can be increased by modifying (e.g., substituting, deleting or adding) amino acid residues identified as involved in the interaction between the Fc region and the FcRn receptor.

All references cited herein, including journal articles or abstracts, patent applications or any other references, are entirely incorporated by reference herein, including all data, tables, figures and text presented in the cited references. Additionally, the entire contents of the references cited within the references cited herein are also entirely incorporated by reference.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation.

DESCRIPTION OF THE FIGURE

FIG. 1 shows an alignment of the amino acid sequences of the variable regions of the variant heavy chains and indicates the differences in amino acid sequences in the framework regions and CDRs among the 2 variants, with the human germline immunoglobulin heavy variable 3-23 (IGHV3-23*01) and with the human germline immunoglobulin heavy chain joining group 4 (IGHJ4*02).

FIG. 2 shows an alignment of the amino acid sequences of the variable regions of the variant light chains and indicates the differences in amino acid sequences in the framework regions and CDRs among the three variants, with the human germline immunoglobulin light variable 1-27 (IGKV1-27*01) and with human germline immunoglobulin kappa joining group 5 (IGKJ5*01).

FIG. 5: Inhibition of CXCL13-stimulated chemotaxis of L1.2 cells expressing-human (panel A to F) and cynomolgus monkey (G and H) CXCR5, caused by anti-CXCR5 40C01-VH1-Vk3 and 40C01-VH2-Vk3 variants expressed in a whole antibody format as IgG1, IgG2 and IgG4. The results were normalized for basal activity (medium alone) and the maximal response obtained with 10 nM CXCL13 (100%). The displayed data are representative of three independent experiments. All points were run in triplicate (error bars indicate +/−S.E.M).

Figure 6A:
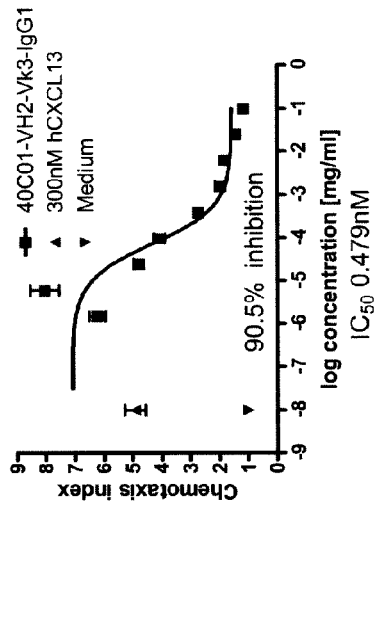
Figure 6B:
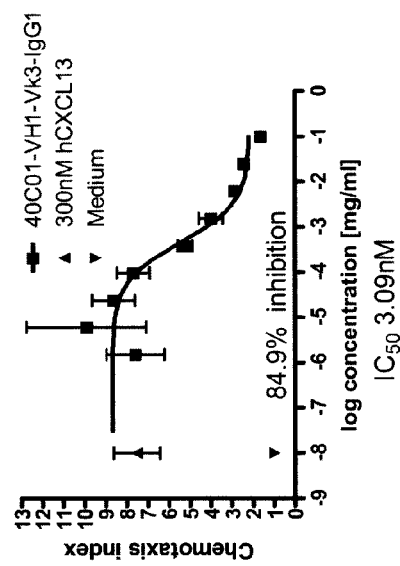

FIG. 6: shows a representative example of inhibition of human CXCL13-stimulated chemotaxis of primary human B cells caused by anti-CXCR5 40C01-VH1-Vk3 (panel A) and 40C01-VH2-Vk3 (panel B) variants expressed in a whole antibody format as IgG1. The results are expressed as calculated $IC_{50}$s (half maximal inhibitory concentration). Values are the means+/−S.E.M from 8 (40C01-VH1-Vk3) and 5 (40C01-VH2-Vk3) separate experiments respectively.

Figure 7A:
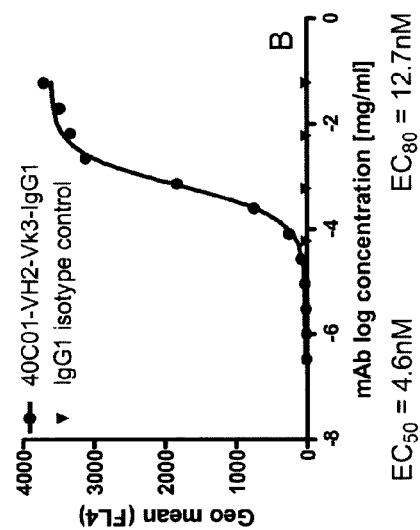
Figure 7B:
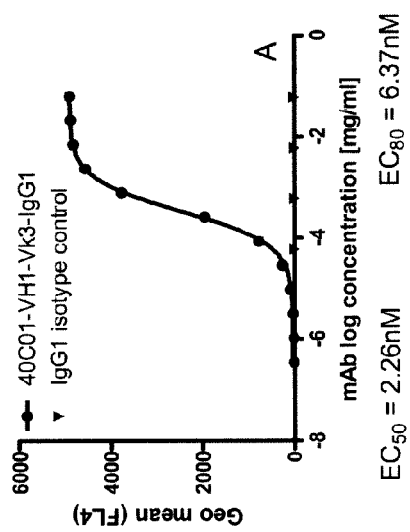

FIG. 7: Binding of Alexa-Fluor 647 labelled anti-CXCR5 40C01 variants to HEK-293 cells stably transfected with human CXCR5

Figure 8A:
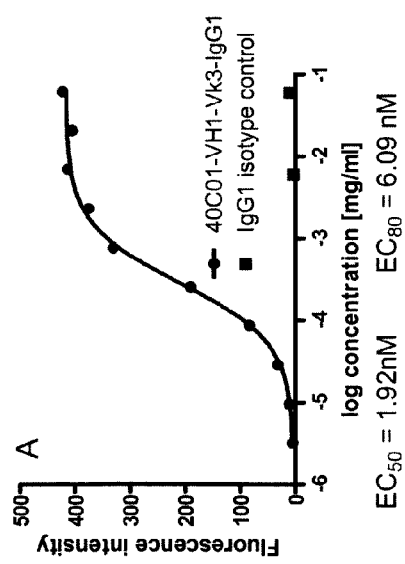
Figure 8B:
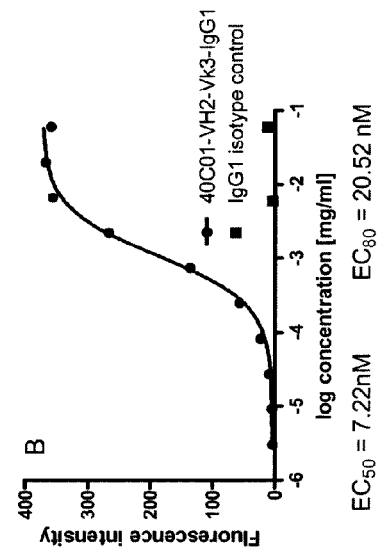

FIG. 8: Binding of Alexa-Fluor 647-labelled anti-CXCR5 40C01 variants to human B cells in whole blood FIG. 9: Binding of anti-CXCR5 40C01 variants to cynomolgus monkey B cells in whole blood FIG. 10: Inhibition of CXCL13-stimulated ERK phosphorylation in B cells in human whole blood by anti-CXCR5 mAbs FIG. 11: Inhibition of CXCL13-stimulated ERK phosphorylation in B cells in cynomolgus monkey whole blood by anti-CXCR5 mAbs FIG. 12: Determination of the $K_D$ of anti-CXCR5 mAb 40C01-VH1-Vk3 variant for cell-membrane expressed CXCR5 using KinExA methodology. CXCR5-HEK-293 cells ($5\times10^6$/ml) were serially diluted and incubated with 30 pM (solid diamonds) or 300 pM (open circles) active binding site concentration of anti-CXCR5 mAb 40C01-VH1-Vk3, in the presence of 0.02% $NaN_3$ and allowed to equilibrate. The free mAb left in the supernatant was measured. (A) The % free mAb is plotted against the antigen concentration (arbitrarily taking each million cells to be equal to $10^{-9}$ M antigen). Multiple curve analysis ("n-curve analysis") using the unknown antigen method was performed to determine optimal values for $K_D$ and the antigen multiplier (B and C respectively) The 95% confidence intervals were determined by iteratively changing the optimized value for $K_D$ or antigen multiplier while keeping other parameters at their optimal values.

Figure 13:
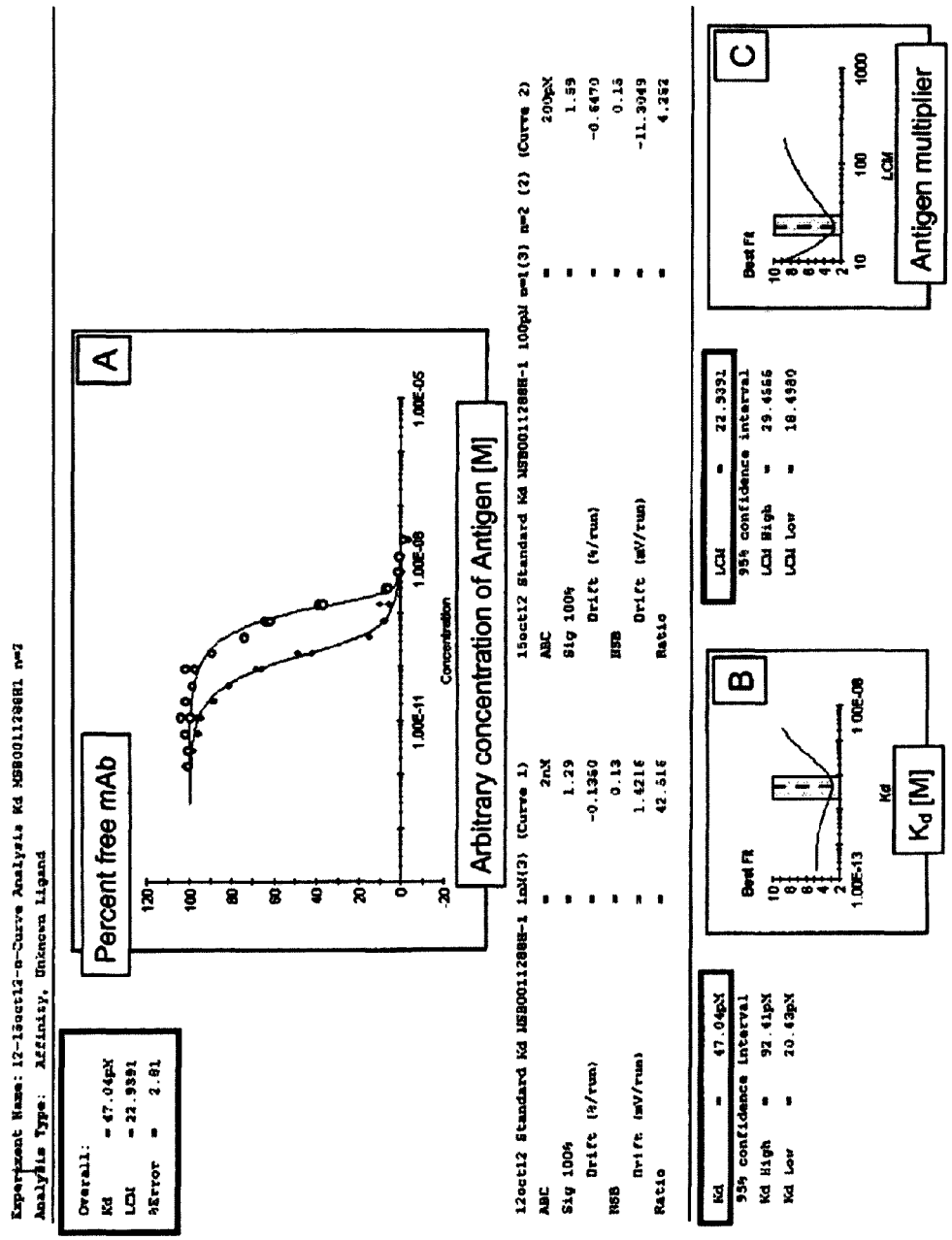

FIG. 13: Determination of the $K_D$ of anti-CXCR5 mAb 40C01-VH2-Vk3 variant for cell-membrane expressed CXCR5 using KinExA methodology. CXCR5-HEK-293 cells ($5\times10^6$/ml) were serially diluted and incubated with 100 pM (solid diamonds) or 1 nM (open circles) active binding site concentration of anti-CXCR5 mAb 40C01-VH1-Vk3, in the presence of 0.02% $NaN_3$ and allowed to equilibrate. The free mAb left in the supernatant was measured. (A) The % free mAb is plotted against the antigen concentration (arbitrarily taking each million cells to be equal to $10^{-9}$ M antigen). Multiple curve analysis ("n-curve analysis") using the unknown antigen method was performed to determine optimal values for $K_D$ and the antigen multiplier (B and C respectively) The 95% confidence intervals were determined by iteratively changing the optimized value for $K_D$ or antigen multiplier while keeping other parameters at their optimal values FIG. 14: Anti-CXCR5-mediated antibody-dependent cell-mediated cytotoxicity (ADCC) of human NK cells purified from peripheral blood mononuclear cells (PBMC's) targeting 51Cr-labelled human B cells.

FIG. 15: Anti-CXCR5-mediated ADCC of human PMBCs targeting 51CR-labelled L1.2 cells expressing either human (panel A) or cynomolgus monkey (panel B) CXCR5. The same effector/target cell mixtures were incubated under the same assay conditions with anti-CXCR5 mAb prepared either with standard glycosylation content (40C01-VH1-Vk3-IgG1) or as an afucosylated antibody (40C01-VH1-Vk3-IgG1_low_fucose).

Figure 16:
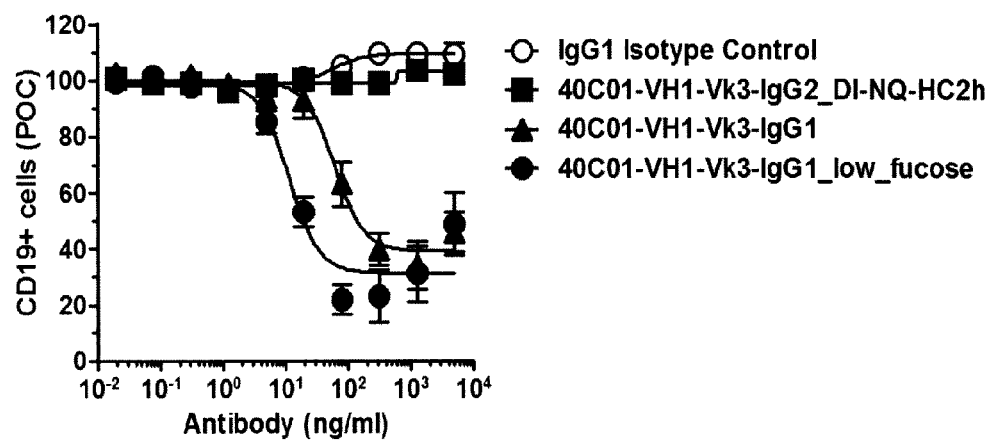

FIG. 16: Depletion of Human B cells induced by anti-CXCR5 antibody. Human PBMCs ($5\times10^6$/ml) were cultured in the presence of a range of concentrations of the indicated antibodies overnight. The percentage of CD19+ B cells in the lymphocyte gate was assessed by flow cytometry from 5 donors. The data was normalized for each donor to the isotype control and combined from 5 donors (POC=percent of control). The mean±SEM are shown.

DESCRIPTION OF THE SEQUENCES

SEQ ID NO:1: Variable heavy chain for the mAbs 40C01 and 12A01 (amino acid sequence)
SEQ ID NO:2: Variable light chain for the mAb 40C01 (amino acid sequence)
SEQ ID NO:3: Variable heavy chain for the mAb 40C01-VH1 (amino acid sequence)
SEQ ID NO:4: Variable heavy chain for the mAb 40C01-VH2 (amino acid sequence)
SEQ ID NO:5: Variable light chain for the mAb 40C01-Vk1 (amino acid sequence)
SEQ ID NO:6: Variable light chain for the mAb 40C01-Vk2 (amino acid sequence)
SEQ ID NO:7: Variable light chain for the mAb 40C01-Vk3 (amino acid sequence)
SEQ ID NOS:8 to 19: CDRs sequence of the mAbs of the series 40C01 (amino acid sequence)
SEQ ID NOS:20 to 34: FRs sequence of the mAbs of the series 40C01 (amino acid sequence)
SEQ ID NO:35: human CXCR5 (amino acid sequence)
SEQ ID NO:36: *Macaca fascicularis* CXCR5 (amino acid sequence)
SEQ ID NO:37: *Macaca mulatta* (amino acid sequence)
SEQ ID NO:38: Heavy chain constant region—human IgG1, allotype G1m(f) (amino acid sequence)
SEQ ID NO:39: Heavy chain constant region—human IgG2 DI-NQ-HC2h subtype (amino acid sequence)
SEQ ID NO:40: Heavy chain constant region—human IgG4 S228P-R409K subtype (amino acid sequence)
SEQ ID NO:41: Variable heavy chain for the mAb 40C01 (nucleic acid sequence). Nucleotides 1 to 60 of this sequence encode the leader sequence.
SEQ ID NO:42: Variable light chain for the mAb 40C01 (nucleic acid sequence). Nucleotides 1 to 60 of this sequence encode the leader sequence.
SEQ ID NO:43: Variable heavy chain for the mAb 40C01-VH1 (nucleic acid sequence). Nucleotides 1 to 57 of this sequence encode the leader sequence.
SEQ ID NO:44: Variable heavy chain for the mAb 40C01-VH1 (codon optimized nucleic acid sequence). Nucleotides 1 to 57 of this sequence encode the leader sequence.

SEQ ID NO:45: Variable heavy chain for the mAb 40C01-VH2 (nucleic acid sequence). Nucleotides 1 to 57 of this sequence encode the leader sequence.
SEQ ID NO:46: Variable heavy chain for the mAb 40C01-VH2 (codon optimized nucleic acid sequence). Nucleotides 1 to 57 of this sequence encode the leader sequence.
SEQ ID NO:47: Variable light chain for the mAb 40C01-Vk1 (nucleic acid sequence). Nucleotides 1 to 60 of this sequence encode the leader sequence.
SEQ ID NO:48: Variable light chain for the mAb 40C01-Vk2 (nucleic acid sequence). Nucleotides 1 to 60 of this sequence encode the leader sequence.
SEQ ID NO:49: Variable light chain for the mAb 40C01-Vk3 (nucleic acid sequence). Nucleotides 1 to 60 of this sequence encode the leader sequence.
SEQ ID NO:50: Variable light chain for the mAb 40C01-Vk3 (codon optimized nucleic acid sequence). Nucleotides 1 to 60 of this sequence encode the leader sequence.
SEQ ID NO:51: Variable heavy chain for the mAb optimized 42F03
SEQ ID NO:52: Variable light chain for the mAb optimized 42F03
SEQ ID NO:53: Variable heavy chain for the mAb 80A10
SEQ ID NO:54: Variable light chain for the mAb 80A10
SEQ ID NO:55: Variable heavy chain for the mAb 80A11
SEQ ID NO:56: Variable light chain for the mAb 80A11
SEQ ID NO:57: Variable heavy chain for the mAb 80B09
SEQ ID NO:58: Variable light chain for the mAb 80B09
SEQ ID NO:59: Variable heavy chain for the mAb 80D11
SEQ ID NO:60: Variable light chain for the mAb 80D11
SEQ ID NO:61: Variable heavy chain for the mAb 42F03
SEQ ID NO:62: Variable light chain for the mAb 42F03
SEQ ID NO:63: Light chain constant region—Lambda constant gene 3 (amino acid sequence)
SEQ ID NO:64: Light chain constant region—Kappa unique constant gene (amino acid sequence)
SEQ ID NO:65: Variable light chain for the mAb 12A01
SEQ ID NO:66: Variable heavy chain for the mAb optimized 42F03 (nucleic acid sequence). Nucleotides 1 to 60 of this sequence encode the leader sequence.
SEQ ID NO:67: Variable light chain for the mAb optimized 42F03 (nucleic acid sequence). Nucleotides 1 to 60 of this sequence encode the leader sequence.
SEQ ID NO:68: Variable light chain for the mAb 80A10 (nucleic acid sequence). Nucleotides 1 to 75 of this sequence encode the leader sequence.
SEQ ID NO:69: Variable heavy chain for the mAb 80A10 (nucleic acid sequence). Nucleotides 1 to 60 of this sequence encode the leader sequence.
SEQ ID NO:70: Variable light chain for the mAb 80A11 (nucleic acid sequence). Nucleotides 1 to 60 of this sequence encode the leader sequence.
SEQ ID NO:71: Variable heavy chain for the mAb 80A11 (nucleic acid sequence). Nucleotides 1 to 60 of this sequence encode the leader sequence.
SEQ ID NO:72: Variable light chain for the mAb 80B09 (nucleic acid sequence). Nucleotides 1 to 60 of this sequence encode the leader sequence.
SEQ ID NO:73: Variable heavy chain for the mAb 80B09 (nucleic acid sequence). Nucleotides 1 to 60 of this sequence encode the leader sequence.
SEQ ID NO:74: Variable light chain for the mAb 80D11 (nucleic acid sequence). Nucleotides 1 to 60 of this sequence encode the leader sequence.
SEQ ID NO:75: Variable heavy chain for the mAb 80D11 (nucleic acid sequence). Nucleotides 1 to 60 of this sequence encode the leader sequence.
SEQ ID NO:76: Variable light chain for the mAb 42F03 (nucleic acid sequence). Nucleotides 1 to 63 of this sequence encode the leader sequence.
SEQ ID NO:77: Variable heavy chain for the mAb 42F03 (nucleic acid sequence). Nucleotides 1 to 60 of this sequence encode the leader sequence.
SEQ ID NO:78: Variable light chain for the mAb 12A01 (nucleic acid sequence). Nucleotides 1 to 60 of this sequence encode the leader sequence.
SEQ ID NO:79: Heavy chain for the mAb 40C01-VH1-IgG1 (amino acid sequence)
SEQ ID NO:80: Heavy chain for the mAb 40C01-VH1-IgG2_DI-NQ-HC2h-subtype (amino acid sequence)
SEQ ID NO:81: Light chain for the mAb 40C01-Vk3-c-Kappa (amino acid sequence)

Example 1

Discovery 1.1. Generation of Stable Cell Lines Expressing Human and Macaque CXCR5

Codon optimized cDNAs encoding human CXCR5 (based on NCBI reference NM_001716.3, encoding an amino acid sequence of SEQ ID NO:35) and cynomolgus monkey (*Macaca fascicularis*) CXCR5 (see SEQ ID NO:36) were generated by gene synthesis, with or without a C-terminal tag. The sequence for *Macaca fascicularis* CXCR5 was not available in public databases. The cDNA sequence was therefore cloned from cynomolgus monkey spleen cDNA (purchased from Biochain) by RT-PCR using degenerate oligonucleotide primers based on the sequences of human CXCR5 and rhesus monkey (*Macaca mulatta*) (NCBI reference XM_001100017.2, encoding an amino acid sequence of SEQ ID NO:37). The full length cDNAs were subcloned into the mammalian cell expression vector pcDNA4 (Invitrogen). Stable cell lines that over-express codon optimized hCXCR5: Chinese hamster ovary cells CHO-hCXCR5; canine thymus cell line Cf2Th-hCXCR5; Hamster fibroblast cell line R1610-hCXCR5; human embryonic kidney cell line HEK293-hCXCR5 and codon optimized *Macaca fascicularis* CXCR5: Chinese hamster ovary cells cCXCR5-CHO were generated by transfection using a commercially available transfection reagent such as Gene Porter (Genlantis). Cells expressing the transfected CXCR5 gene were selected with neomycin (G418). Stable clones resistant to neomycin, expressing high levels of CXCR5 on the cell surface were identified by FACs analysis using a commercially available anti-CXCR5 mAb (mAb 190, R&D systems).

1.2. Preparation of Paramagnetic Proteoliposomes (PMPLs) Expressing CXCR5

Paramagnetic Proteoliposomes (PMPLs) containing human or *Macaca fascicularis* CXCR5 were prepared by MSM Protein Technologies using MSM's proprietary technology based on the method described by Mirzabekov et al., (2000). In brief, cells that over-expressed CXCR5 were harvested, and membranes of the cells were solubilized in a proprietary mixture of detergents. The surface of non-porous paramagnetic beads was covalently conjugated with streptavidin and an antibody that recognizes the C-terminal tag on the CXCR5. The conjugated beads were used to capture the C-terminally-tagged CXCR5 from the solubilized cell lysates. After extensive washing to remove contaminants, the beads were mixed with detergent-solubilized lipid containing 0.1-1% of Biotinyl-DOPE. Detergent was removed by dialysis, during which the lipid bilayer membrane selfassembles around the beads and CXCR5 is returned to its native environment. A commercial anti-hCXCR5-PE conjugated antibody (R&D systems) was used to demonstrate that the beads contained CXCR5 in the correct orientation (i.e. the extracellular portion exposed on the surface of the bead) by Guava® easy Cyte flow cytometry (Millipore). The conditions used for generating hCXCR5-PMPLs were also used to generate PMPLs for *Macaca fascicularis* CXCR5.

1.3. Generation of Anti-CXCR5 Antibodies Using Phage Display Technology.

Phage display technology was used to identify neutralizing antibodies against CXCR5 from a human Fab-phage 410 antibody library from DYAX using PMPLs bearing CXCR5 as target. Several different selection arms were employed to select Fabs binding specifically to human CXCR5 (4-5 rounds of selection) or cross-reactive Fabs binding to human and *Macaca fascicularis* CXCR5 using alternating rounds of selection against the human and *Macaca fascicularis* CXCR5.

Fabs isolated from approximately 9535 clones from the round 3 selection outputs were reformatted into the expression vector pXP1s-SacB (DYAX) and expressed in *E. coli* BL21 Gold cells in 96 or 24 well plates after induction with IPTG (100 µM) for 18 h, essentially as previously described by Hoet et al., (2005). Culture medium containing the soluble secreted Fabs was screened by incubating with human or *Macaca fascicularis* over-expressing CXCR5 cell lines for 40 min at room temperature (RT). Unbound Fabs were washed away then cells were incubated with an anti-c-Myc mouse monoclonal antibody (9E10) for 20 min at RT. Unbound antibody was washed away and cells were incubated with anti-mouse IgG-PE labelled secondary antibody for 20 min at RT. The cells were then washed twice, fixed, and analyzed using a Guava® FACS plate reader.

973 Clones that displayed human-*Macaca fascicularis* CXCR5 cross-reactivity were identified. Upon sequence analysis 168 unique sequences were identified of which 46 had unique heavy chain CDR3 sequences (data not shown). All clones of interest were then reformatted as full human IgG1 in the mammalian cell expression vector pTT5, (National Research Council of Canada, see application US20110039339), transiently expressed in HEK293 cells, and purified for testing in cell based assays.

1.4. Antibody Expression and Purification

Antibody heavy and light chains were subcloned separately into the pTT5 vector and were transiently co-expressed in HEK293 cells adapted to suspension culture, after transfection using Polyethyleneimine (PEI) transfection reagent. Cells were incubated for 3 days with shaking at 37° C. in a 5% $CO_2$ humidified incubator. Conditioned medium was harvested and centrifuged to remove cell debris. Antibodies were purified from culture supernatants by Protein A affinity chromatography using standard methods, desalted on Sephadex G25 and formulated in PBS for all assays except the FLIPR calcium assay, for which the antibodies were formulated in TBS. For large scale antibody preparations (>400 ml cultures) an additional size exclusion chromatography (SEC) step was performed on Superdex-200 resin to remove aggregates. The following QC analysis was performed on the purified proteins: SDS PAGE under reducing and non-reducing conditions: SEC for determination of purity and apparent MW; UV spectroscopy for concentration determination. Measurement of endotoxin contamination was performed using the Endosafe PTS assay. One to 5 mg of purified antibody was typically obtained from 50 ml cultures.

1.5. Cell-Based Binding Assays for Anti-CXCR5 Fabs

Binding of anti-CXCR5 antibodies to cell lines and primary cells expressing human CXCR5 or species orthologues was assessed by FACS. Briefly, approximately $1 \times 10^5$ CXCR5 expressing cells were suspended in FACS buffer (PBS containing 1% FBS and 0.02% sodium azide) containing increasing concentrations of anti-CXCR5 antibodies ranging from 0-100 µg/ml, and incubated for 20 min at 4° C. Cells were washed and then resuspended in FACS buffer containing PE-labelled goat anti-human IgG (Jackson labs) for 20 min at 4° C. Cells were then washed 3 times and resuspended in 100 µl FACS buffer and analysed on a FACScalibur instrument (BD Sciences). MFI was plotted against antibody concentration and Graph pad prism software was used to calculate $EC_{50}$ values.

The mAbs 80A11, 80A10, 80B09 were highly specific for human CXCR5 (data not shown). 42F03, 12A01, 40C01 and 80D11 bound to both human and *Macaca fascicularis* CXCR5 (data not shown). None of the antibodies identified in example 1.3 were cross reactive with rat or mouse CXCR5.

1.6. FLIPR Calcium Mobilization Assay

The ability of the anti-CXCR5 to inhibit mobilization of intracellular calcium (calcium flux) induced by CXCL13 in CXCR5 expressing cells was determined in a FLIPR assay using the Calcium 5 Assay Kit (Molecular Devices). R1610-hCXCR5 cells were plated at 40,000-60,000 cells per well in a 96-well flat bottom tissue culture plate in CHO-S-SFM II serum-free culture media (Gibco) and incubated overnight at 37° C., in a humidified 5% $CO_2$ incubator to allow cells to attach to the bottom of the well and form a monolayer with confluency close to 100%. Cells were loaded with dye according to the kit manufacturer's protocol, then pre-incubated with increasing concentrations (up to 1 µM) of anti-CXCR5 antibodies for 1 h at 37° C., washed, then exposed to 130 nM CXCL13. Changes in calcium flux were monitored on a Molecular Devices FLEXstation III instrument. All antibodies identified in example 1.5 were able to inhibit CXCL13-induced intracellular calcium flux (data not shown).

1.7. Chemotaxis Assay

The ability of anti-CXCR5 antibodies to inhibit CXCL13-induced migration of L1.2 cells over expressing CXCR5, was determined in a chemotaxis assay system. A mouse pre-B cell line L1.2, stably transfected with human or *Macaca fascicularis* CXCR5 was generated for this purpose. L1.2 cells maintained in RPMI medium containing 5% heat inactivated FCS, 2 mM glutamine and 50 µM-mercaptoethanol were transfected by electroporation with human or *Macaca fascicularis* CXCR5 cDNA cloned into the mammalian cell expression vector pcDNA3.1 hygro DEST (Invitrogen). Cells expressing CXCR5 were selected in medium containing 600 µg/ml hygromycin, and after 12-14 days were subjected to single cell cloning by seeding cells at 0.3 cell/well in 96-well tissue culture plates. Clones which grew up were tested for CXCR5 expression by FACs using an anti-CXCR5 antibody from R&D systems (mAb 190). One clone expressing high levels of CXCR5 (L1.2/CXCR5 clone 19) was expanded for further use.

For the chemotaxis assay L1.2/CXCR5 cells were suspended at $0.7 \times 10^6$ cells/ml and incubated with increasing concentrations of anti-CXCR5 antibodies (from 0-1.0 µM) for 30 min at 37° C. The cells were then added to the top chamber of a Neuroprobe ChemoTx 96 well chemotaxis system with 8 µm pore size filter, which contained 10 nM CXCL13 in the bottom microplate chamber. The assembly was covered with a lid and incubated at 37° C. in a humidified air incubator pulsed with 5% $CO_2$ for 5 h. After 5 h, the filter was removed and migrated cells in the lower chamber were transferred into a 96 well, flat bottom, black plate according to the manufacturer's instructions. After transfer, the black plate was sealed and placed in a –80° C. freezer for 1-2 h or overnight, to freeze the cells. Cells were then thawed at RT for 20 min and stained with CyQuant (Invitrogen). Fluorescence was measured on a Synergy™ H4 microplate reader (Bio Tek Instruments). Fluorescence is proportional to the number of migrated cells. The chemotactic index was calculated for each sample (fluorescence signal in response to CXCL13/fluorescence signal of cells migrating spontaneously in the absence of chemokine) and plotted as a function of the concentration of anti-CXCR5 antibody. $IC_{50}$ values were determined using GraphPad prism software.

Of 46 clones with unique heavy chain CDR3 identified in example 1.3, 42 were successfully reformatted and expressed as IgG1. At least twelve clones were able to neutralize CXCL13 induced L1.2/CXCR5 cell chemotaxis with $IC_{50}$ values ranging between 1-2200 nM (see table 1).

Example 2

Optimization of mAb 40C01

2.1. Heavy and Light Chain Variants

The amino acid sequences of the variable regions of the 40C01 heavy (SEQ ID NO:1; VH) and light (SEQ ID NO:2; VL) chains were separately modified, by altering both framework region and CDR sequences in the heavy and light chain variable regions. The purpose of these sequence alterations was either to mutate framework amino acid residues to the most homologous human germline residue found at that position, to increase potency in relevant cellular assay, to improve manufacturability of the molecule by preventing Asp isomerization, Asn deamidation and Met oxidation, or to deplete the antibody of in silico identified human T-cell epitopes, thereby reducing or abolishing its potential immunogenicity in humans.

Two heavy-chain variants (SEQ ID NOs: 3 and 4) were constructed, as a human IgG1, IgG4 (containing a S241P amino acid change that stabilizes the hinge domain (Angal et al., 1993) and the allotype with Lys at position 409) or modified IgG2 (subtype HC2h, as described in WO2009010290) heavy chain isotypes and are denoted VH1 (corresponding to SEQ ID NO:3) and VH2 (corresponding to SEQ ID NO:4). VH1 and VH2 comprise the following mutations (according to Kabat numbering; residues that are underlined are located in one of the CDRs):

VH1: D46E-D61A-M89V,
VH2: Y32S-D46E-D61A-M89V-M99K

Three light-chain variants were constructed, in a human Kappa chain background, and are denoted Vk1, Vk2 and Vk3. Vk1, Vk2 and Vk3 comprise the following mutations (according to Kabat numbering; as above, residues that are underlined are located in one of the CDRs):

Vk1: K6Q-A7S-D9S-I31A-M48I-H49Y-A51T-R65S-N76S-A80P (see also SEQ ID NO:5),
Vk2: R6Q-A7S-D9S-I31A-A43V-M48I-H49Y-A51T-R65S-N76S-A80P (see also SEQ ID NO:6),
Vk3: R6Q-A7S-D9S-I31A-A43V-M48I-H49Y-A51T-R65S-N76S-A80P-S93A (see also SEQ ID NO:7)

The original and variant heavy and light chains were combined in all possible pair-wise combinations to generate a number of functional fully human anti-CXCR5 antibodies.

2.2. Differential Scanning Calorimetry (DSC) Measurements.

The stability of multi-domain proteins like monoclonal antibodies is commonly investigated using differential scanning calorimetry (DSC, see examples). One of the great advantages is that it can be used for fine-tuning of interactions between the individual domains of a protein. Temperature-induced unfolding of monoclonal antibodies measured by DSC has become an indispensable tool used for monitoring protein structure. Consequently, correct interpretation of the observed transitions is essential.

Temperature-induced unfolding of four IgG1 monoclonal antibodies was monitored by DSC at neutral pH. The profile of the thermograms obtained is showed in FIG. 3. All four thermograms of the intact antibodies present two peaks. For both the control IgG1 isotype and the original 40C01-VH-VL antibody the unfolding presents two transitions with the melting temperatures (Tm) around 71° C. and 83° C., and with the amplitude of the first peak much larger than that of the second peak. Based on the results of studies comparing the DSC profile of an intact IgG and its isolated Fab and Fc fragments (Ionescu et al., 2008), it can be inferred that the first unfolding event in these intact two antibodies is associated with the melting of the CH2 domain in the Fc fragment and the melting of the Fab fragment, while the second transition represents mainly the unfolding of the CH3 domain. This approach relies on the assumption that the Fab fragment unfolds in a cooperative manner, that is, only one transition is observed in the thermogram of the Fab fragment.

For the 40C01 VH1-Vk1 variant, the thermogram has the same profile but with a higher Tm around 74.5° C. for the first peak. For the 40C01 VH1-Vk2 variant, the DSC thermogram has a different melting profile with the amplitude of the second peak, with a Tm of around 83° C., much larger than that of the first peak, with a Tm of around 72° C. Because the peak area in the DSC thermogram represents the experimental enthalpy of unfolding, it can be inferred that in this example the second peak represents the Fab fragment and CH3 domain of the Fc fragment unfolding, while the first peak represents mainly the unfolding of the CH2 domain.

Figure 3:
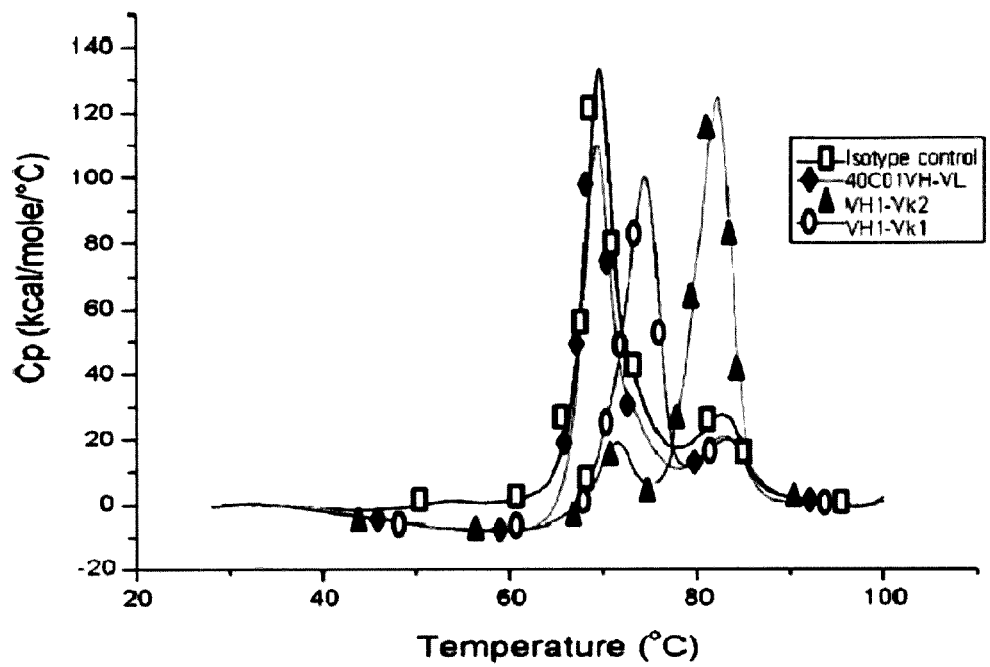
FIG. 3: DSC analysis results for 3 forms of 40C01 mAb (40C01VH-VL, 40C01VH1-Vk1 and 40C01VH1-Vk2). Thermal unfolding curves of four fully human IgG1 antibodies, anti-CXCR5 40C01 parental molecule (40C01 VH-VL), anti-CXCR5 40C01 heavy chain variant 1 paired with light chain variant 1 (VH1-Vk1), anti-CXCR5 40C01 heavy chain variant 1 paired with light chain variant 2 (VH2-Vk2) and an isotype control. The unfolding transitions of the CH2 and CH3 domains for all four IgG1 constructs are identical while the Fab unfolding transitions are highly variable.

In FIG. 3, the DSC analysis shows that the Tm of the Fab fragment has increased from 71° C. in the original 40C01 antibody to around 74.5° C. in the VH1-Vk1 variant, and to 83° C. for the VH1-Vk2 variant. Low stability or heterogeneity of the Fab fragment may prove problematic for long-term storage or consistency of production. Therefore, having a Fab fragment with a Tm of around 83° C. can be seen as beneficial for the development of this therapeutic monoclonal antibody. This change in the Tm of the Fab fragment demonstrates that its stability is significantly affected by the sequence of the variable heavy and light chain domains. Therefore the changes in the heavy chain and light chain framework and CDR residues which occurred between 40C01 VH and VH1 variant for the heavy chain and between 40C01 VH, Vk1 and Vk2 variant for the light chain, have increased the overall thermal stability of the molecule by fine-tuning the interactions between the VH and VL domains.

Figure 4:
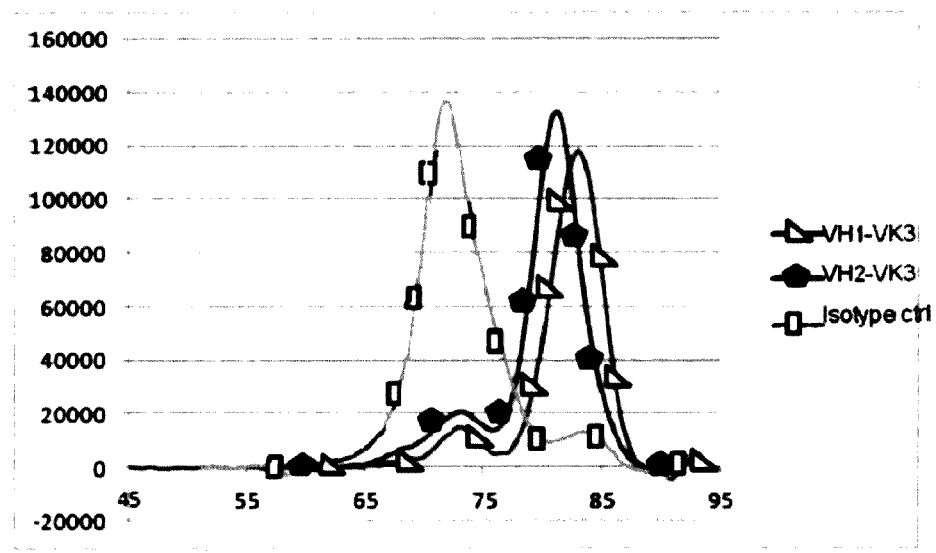
FIG. 4: Thermogram profiles obtained for 40C01VH1-Vk3 and 40C01VH2-Vk3 variants. Thermal unfolding curves of three fully human IgG1 antibodies, anti-CXCR5 40C01 heavy chain variant 1 paired with light chain variant 3 (VH1-Vk3), anti-CXCR5 40C01 heavy chain variant 2 paired with light chain variant 3 (VH2-Vk3) and an isotype control. The unfolding transitions of the CH2 and CH3 domains for all four IgG1 constructs are identical while the Fab unfolding transitions for both anti-CXCR5 40C01 variants are much higher (above 80° C.) than for the isotype control.
Figure 5C:
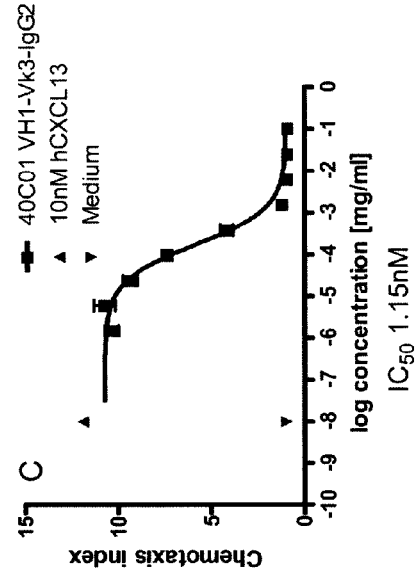
Figure 5D:
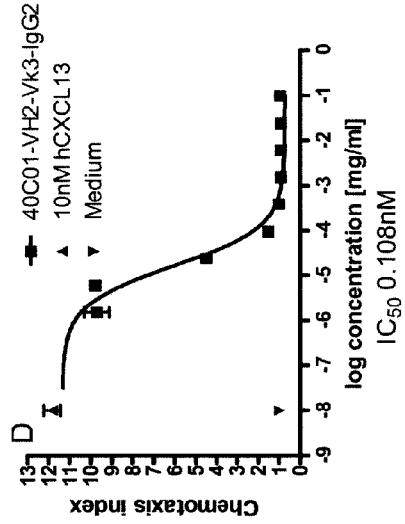
Figure 5A:
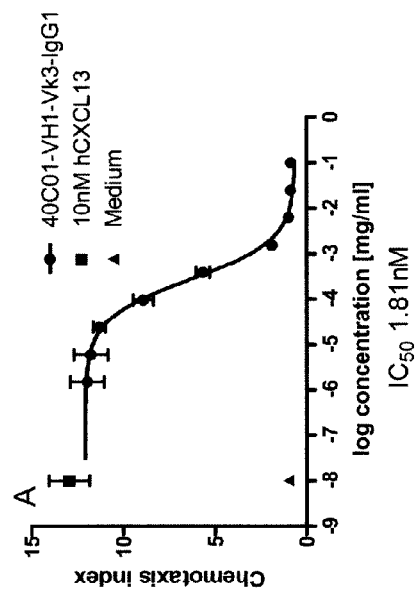
Figure 5B:
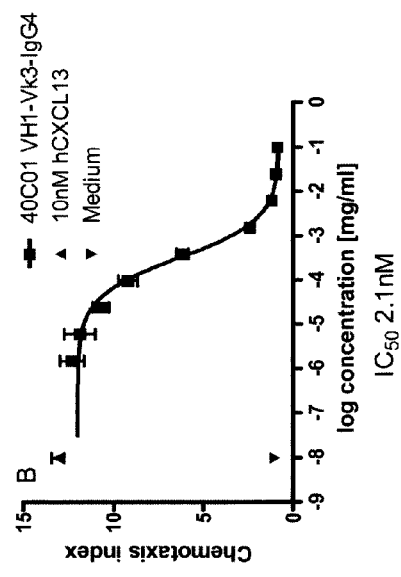
Figure 5E:
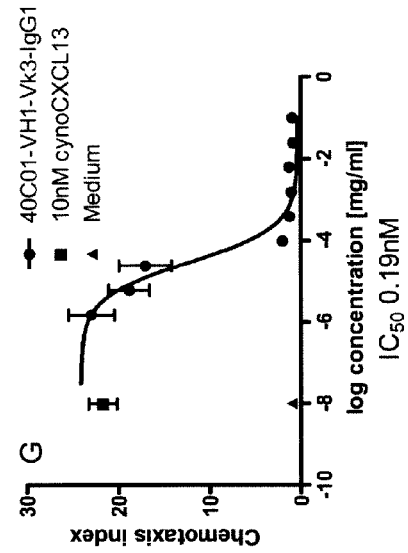
Figure 5G:
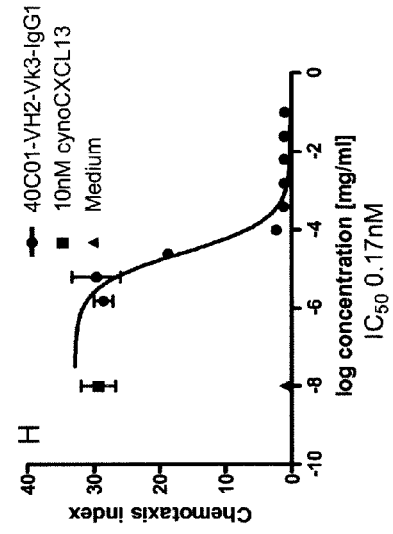
Figure 5F:
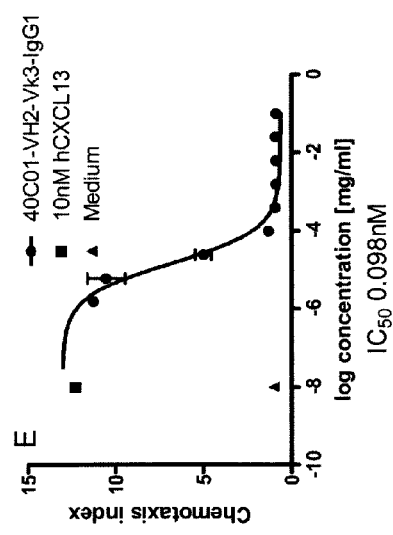
Figure 5H:
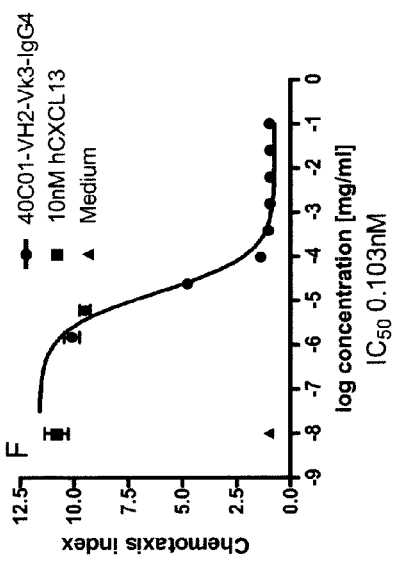

The profile of the thermograms obtained for 40C01 VH1-Vk3 and VH2-Vk3 variants is shown in FIG. 4. Their DSC thermograms have the same melting profiles as the 40C01 VH1-Vk2 variant, with the amplitude of the first peak much smaller than that of the second peak. The first unfolding event is associated with the melting of the CH2 domain in the Fc fragment and the second unfolding event is associated with the melting of the Fab fragment and the CH3 domain in the Fc fragment. For the 40C01 VH1-Vk3 and VH2-Vk3 variants the Tm corresponding to the first and second peaks are around 72° C. and 82° C. and 72° C. and 81° C., respectively. The deduced high Tm values of above 81° C. for the Fab fragments calculated from the thermograms obtained with the full length intact IgG1 molecules were confirmed by the Tm values obtained for the corresponding recombinant Fab fragments produced in mammalian cell expression system. The Tm obtained by DSC for the recombinant Fab fragments of 40C01-VH1-Vk3 and 40C01-VH2-Vk3 were 85.5° C. and 84.1° C., respectively (data not shown).

2.3. Inhibition of CXCL13-Stimulated L1.2-CXCR5 Cell Chemotaxis

A similar protocol to the one disclosed in example 1.7 was followed.

FIG. 5 shows inhibition of CXCL13-stimulated chemotaxis of L1.2-human and *Macaca fascicularis* CXCR5 by anti-CXCR5 40C01-VH1-Vk3 and 40C01-VH2-Vk3 variants expressed in a whole antibody format as IgG1, IgG2 and IgG4. The calculated $IC_{50}$s (half maximal inhibitory concentration) are summarized in Table 2. All mAbs tested inhibited the chemotaxis with 100% efficacy. No difference in potency was seen between the different IgG isotypes for human CXCR5. For human CXCR5, 40C01-VH2-Vk3 variant has a 10 to 20 fold higher potency ($IC_{50}$ in subnanomolar range) than 40C01-VH1-Vk3 variant (single digit nanomolar range) whereas for cynomolgus monkey CXCR5, the variants are equipotent (subnanomolar range).

The binding strength of a univalent antigen to a single combining site on a divalent IgG antibody is defined as affinity. In solution, the binding of each combining site of an IgG antibody to a univalent antigen is independent. However, when the movement of an antigen is partially restricted, as on a cell membrane, epitopes on antigens like CXCR5 may become spatially proximal to both IgG combining sites and the binding of one site may increase the binding strength of the other combining site. The sum of the strength of all binding sites between an antibody and an antigen is defined as avidity. Avidity is influenced by both the valency of the antibody and the valency of the antigen. Avidity can be more than the sum of the individual affinities.

To test if the avidity of the anti-CXCR5 40C01 variants played a role in the strength of the inhibition of chemotaxis, recombinant Fab fragments of 40C01-VH1-Vk3 and VH2-Vk3 variants were tested for inhibition of human CXCR5-L1.2 cell chemotaxis. We found that the recombinant Fab fragments of 40C01-VH1-Vk3 and VH2-Vk3 had $IC_{50}$s of 288 nM and 20.9, respectively; whereas their corresponding full-length human IgG1 had $IC_{50}$s of 0.38 nM and 0.05, respectively. These differences in potency of inhibition of chemotaxis between the intact IgG and their Fab fragments clearly indicate that the bivalency of the IgG is an important factor (data not shown).

2.4. Inhibition of Human Primary B Cell Chemotaxis Induced by CXCL13 in Human Serum Human lymphocytes were isolated from a buffy coat using Ficoll-Paque Plus (GE Healthcare Life Sciences, cat#17-1440-03). B cells were purified by negative selection using MagCellect human B cell isolation kit (R&D Systems, cat# MAGH103). The purified B cells were resuspended in B cell medium (RPMI1640 containing 2 mM Glutamine, 1% non-essential amino acids, 1% sodium pyruvate, 25 mg/ml Pen-Strep, 50 μM β-mercaptoethanol and 10% heat inactivated FCS) at $3 \times 10^6$ cells/ml and kept O/N at 4° C. to overcome possible in vivo desensitization (Hausdorff et al 1990; Tomhave E D 1994) and therefore increase the number of migrating cells. The B cells were then preincubated with serial 1 in 4 dilutions of 40C01 variants starting at 100 μg/ml to 0.38 ng/ml for 20 min at 37° C. in 100% non heat inactivated human serum (PAA Laboratories, cat# C11-020). Migration of human B cells to 300 nM human chemokine CXCL13 (produced in-house) was evaluated using the ChemoTx® System with 5-μm pore size 96-well chemotaxis plates (ChemoTx#101-5, Neuro Probe). Chemotaxis was allowed to proceed at 37° C. in a humidified incubator with 5% $CO_2$ for 2 h. Migrated cells were then transferred to a fresh 96-well microplate, stored at −80° C. for few hours, thawed, stained with CyQuant® (Life Technologies, cat #C7026) and counted. Percentage inhibition was calculated using the following formula: percent of inhibition=100×(1−average cell number under treatment of Abs/average cell number without treatment).

Results are expressed as percentage of control (i.e., CXCL13-induced) migration using the following equation: % M d=(Mab+CXCL13−Mbuffer/Mcxcl13−Mbuffer)×100; where M is migration, Mab+cxcl13 is migration due to antibody+cxcl13, Mbuffer is mean migration due to buffer alone, and Mcxcl13 is mean migration due to cxcl13 alone. The number of cells migrating in the presence of CXCL13 is 100%. It should be noted that basal migration was minimal (~0.5% of the maximal response obtained with CXCL13).

FIG. 6 shows that for the 40C01-VH1-Vk3 variant the mean $IC_{50}$ was 1.89 nM, and ranged from 0.29 to 3.09 nM with a percentage of inhibition ranging from 71 to 88.5%. For the 40C01-VH2-Vk3 variant the mean $IC_{50}$ was 0.34 nM ranging from 0.082 to 0.479 with a percentage of inhibition ranging from 80.8 to 90.5%.

2.5. Binding of Alexa-Fluor 647 Labelled mAbs to Human CXCR5 Stably Transfected HEK-293 Cells Anti-CXCR5 40C01-VH1-Vk3 and VH2-Vk3 variants were labelled with Alexa Fluor 647 dye using monoclonal antibody labelling kit from Invitrogen (Cat #A20186). Binding of labelled mAbs to HEK-293 cells stably transfected with human CXCR5 was examined by a direct immunofluorescence assay. A total of $1 \times 10^5$ stable HEK-293 cells over-expressing human CXCR5 were incubated with 1 in 3 serially diluted Alexa Fluor 647 mAbs ranging from 60 μg/ml to 0.33 ng/ml in FACS buffer (PBS containing 1% BSA and 0.1% $NaN_3$) for 1 h on ice. Cells were washed twice with FACS buffer and analyzed on FACSCalbur flow cytometer (BD Biosciences). The $EC_{50}$ (concentration of Ab that reaches half-maximal cell binding (%) and geometric mean fluorescence intensity (Geo mean), respectively and $EC_{80}$ were calculated by plotting the FL4 fluorescence (emission of Alexa Fluor 647 dye) as a function of the antibody concentration. These $EC_{50}$ and $EC_{80}$ values were used as a measure of the relative binding affinity of each variant to human CXCR5 positive cells. From the results presented in FIG. 7 we calculated $EC_{50}$ values of 2.26 nM and 4.6 nM for 40C01-VH1-Vk3 and VH2-Vk3, respectively.

2.6. Binding of Alexa-Fluor 647 Labeled mAbs to Human B Cells in Whole Blood

40C01-VH1-Vk3 and VH2-Vk3 variants were labelled with Alexa Fluor 647 dye using monoclonal antibody labelling kit from Invitrogen (Cat #A20186). Blood was collected in sodium-heparinised tubes and rested for 2 h at RT. Sodium azide ($NaN_3$) was then added to whole blood to a final concentration of 0.01%. Serial 1 in 3 dilutions of Alexa-Fluor 647 labelled-mAbs ranging from 60 μg/ml to 3 ng/ml were added to blood samples and incubated for 30 min at RT.

Phycoerythrin (PE) labelled anti-CD19 (BD Pharmingen, cat#555413) and anti-human CXCR2 (R&D Systems, cat #FAB331P) mAbs and their respective isotype controls were used for gating B cells and monitoring CXCR2 expression on granulocytes, respectively. Labelled red blood cells were then lysed using the human erythrocyte lysing kit from R&D Systems (Cat # WL1000) and the blood cells resuspended in FACS buffer (PBS-1% BSA, 0.1% $NaN_3$) and analysed by flow cytometry on FACS Calibur 3 (BD Biosciences). The $EC_{50}$ and $EC_B$, values were calculated by plotting the FL4 fluorescence (emission of Alexa Fluor 647 dye) as a function of the antibody concentration. From the results presented in FIG. 8 we calculated $EC_{50}$ values of 1.92 nM and 7.22 nM for 40C01-VH1-Vk3 and VH2-Vk3, respectively. No binding of the two 40C01 variants was detected on the granulocyte population which expresses CXCR2 (neutrophils).

Figure 9:
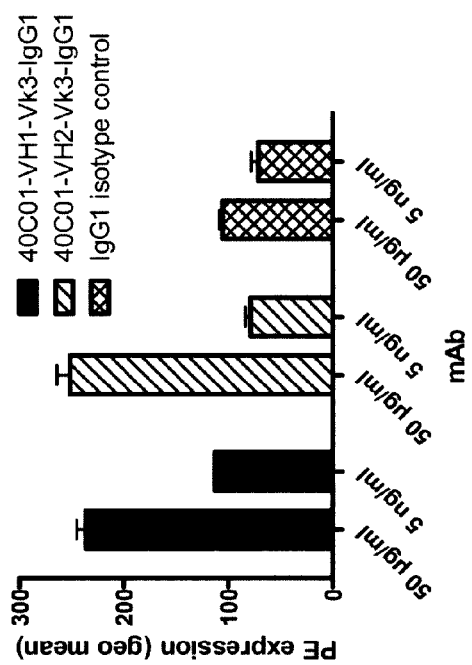

2.7. Binding of Anti-CXCR5 40C01 Variants to Cynomolgus Monkey B Cells in Whole Blood Cynomolgus monkey (*Macaca fascicularis*) blood was collected in sodium-heparinised tubes and stored at RT. Sodium azide ($NaN_3$) was added to the blood to a final concentration of 0.01%. 5 µl dilutions of antibodies at 500 µg/ml and 50 ng/ml were added in duplicate to 45 µl of blood and incubated for 30 min at RT. Red blood cells were then lysed using the human erythrocyte lysing kit from R&D Systems (Cat # WL1000). Fc receptors were blocked using Fc receptor blocker from Innovex (cat # NB309). Phycoerythrin (PE)-conjugated goat anti-human Fc fragments (Jackson Immuno Research, cat#109-116-098) and allophycocyanin (APC)-conjugated mouse IgG2b anti-human CD20 (BD Biosciences, cat #559776) and their respective isotype controls were used to detect binding of anti-CXCR5 40C01-VH1-Vk3 and VH2-Vk3 variant mAbs and for gating B cells, respectively. After 30 min incubation on ice, the blood cells were washed, resuspended in FACS buffer (PBS containing 1% BSA and 0.1% $NaN_3$) and analysed by flow cytometry on a FACS Calibur 3 (BD Biosciences). The results presented in FIG. 9 show that at 50 µg/ml, both 40C01 variants exhibit a strong and specific binding to cynomolgus monkey CXCR5 expressed on B cells 2.8. Inhibition of CXCL13-Stimulated ERK Phosphorylation in B Cells from Human and Cynomolgus Monkey Whole Blood by Anti-CXCR5 mAbs The binding of CXCL13 to its chemokine receptor CXCR5 triggers several intracellular signalling events and in particular transient phosphorylation (activation) of the p44/42 mitogen-activated protein (MAP) kinase (extracellular signal-regulated kinases; ERK1/2). This assay measures the inhibition of CXCL13 stimulated ERK phosphorylation in B cells in whole blood by anti-CXCR5 40C01 variants, using flow cytometry.

Blood is collected in sodium-heparinised tubes and rested for 2 h at RT. Serial dilution of antibodies are added to the blood and incubated for 30 min at 37° C. B cells in whole blood are then activated with 500 nM human or 350 nM cynomolgus monkey CXCL13 at 37° C. The signalling activation is stopped after 2 min by fixation of cells in 4% formaldehyde for 8 min at RT. After fixation, Triton X-100 was added to a final concentration of 0.1% and incubated at 37° C. for 35 min. The cells are washed with PBS, fixed with methanol (50% final concentration) and incubated at −20° C. for at least 1 h. The cells are then left on the bench to warm-up to RT, washed, and a 1/50 dilution of anti-Phospho-p44/42 MAPK (ERK1/2) rabbit antibody (Cell Signaling Technology, cat#4370S) in FACS staining buffer (PBS containing 4% FCS) added and incubated for a further 1 h at RT. The cells were then washed with FACS staining buffer and a mix of 1/400 dilution of Alexa Fluor 647 donkey anti-rabbit IgG (Invitrogen. Cat# A31573) and 1/2.5 dilution of anti-human CD20-PE (BD Pharmingen, Cat#556633) antibodies added and incubated for 1 h on ice. The cells were then washed and resuspended in FACS staining buffer and analysed by flow cytometry. The phospho-ERK fluorescence histogram gated on CD20+ cells is displayed (FL4) (data not shown). For each sample the percentage positive cells is reported. The percentages of positive cells are represented as a function of the concentration of anti-CXCR5 mAbs and $IC_{50}$s calculated. From the results presented in FIG. 10, for human blood the calculated $IC_{50}$s for 40C01-VH1-Vk3 as IgG1 and IgG2 were 0.17 nM (panel D) and 0.736 nM (panel A), respectively; and for 40C01-VH2-Vk3 as IgG1 and IgG2 were 0.45 nM (panel C) and 0.88 nM (panel B), respectively. From the results obtained in FIG. 11 for cynomolgus monkey blood, the calculated $IC_{50}$s for 40C01-VH1-Vk3 and 40C01-VH2-Vk3 both as IgG1 were 0.195 nM and 1.57 nM, respectively. The results obtained are summarized in Table 3.

2.9. Determination of the $K_d$ of Anti-CXCR5 mAb Variants for Cell-Membrane Expressed CXCR5

Kinetic Exclusion Assay (KinExA) was used to determine the concentration of the free antibody that remains in solution after equilibrium has been established between the fully human IgG2 (subtype HC2h, as described in WO2009010290) anti-CXCR5 40C01 antibody variants and human CXCR5 expressed on the cell surface of stably transfected HEK-293 cells, from which the equilibrium dissociation constant (Kd) was determined. This method provides a true measure of the affinity/avidity of the antibody to integral membrane proteins like GPCRs.

HEK-293 cells, stably expressing human CXCR5, an integral membrane protein with 7 trans membrane domains, were harvested using Accutase cell detachment solution, resuspended at $2 \times 10^6$ cells/ml and serially diluted 1 in 2 in 15 falcon tubes using KinExA buffer (PBS containing 1 mg/ml BSA and 0.02% $NaN_3$). An appropriate constant concentration of purified mAb was made in KinExA buffer and an equal volume of the mAb was mixed with the serially diluted cells. To obtain the standard Kd values, two different concentrations of mAbs were tested, 30 µM and 300 µM for 40C01-VH1-Vk3 variant and 100 µM and 1 M for 40C01-VH2-Vk3 variant. The cells were mixed with the mAb by rotation for at least 24 h at RT. The cells were then centrifuged and the free mAb present in the supernatant was measured by KinExA using PMMA beads (Sapidyne Instruments, cat#440198) coated with goat anti-human IgG (H+L) (Jackson ImmunoResearch, cat#109-005-003) and DyLight 649-conjugated anti-human secondary antibody (Jackson ImmunoResearch, Goat anti-human Fc, cat#109-495-098) used at 1 µg/ml in KinExA buffer. The standard Kd was obtained using KinExA software and by "n-curve analysis" which fits the curves obtained at 30 µM and 300 pM for 40C01-VH1-Vk3 and 100 µM and 1 nM for 40'C01-VH2-Vk3, to a single Kd value simultaneously. The percentage of free mAb left in solution was plotted against the concentration of antigen (arbitrarily defined as 1 nM of antigen per 1 million cells) using the KinExA software and a sigmoidal curve was generated.

Figure 12:
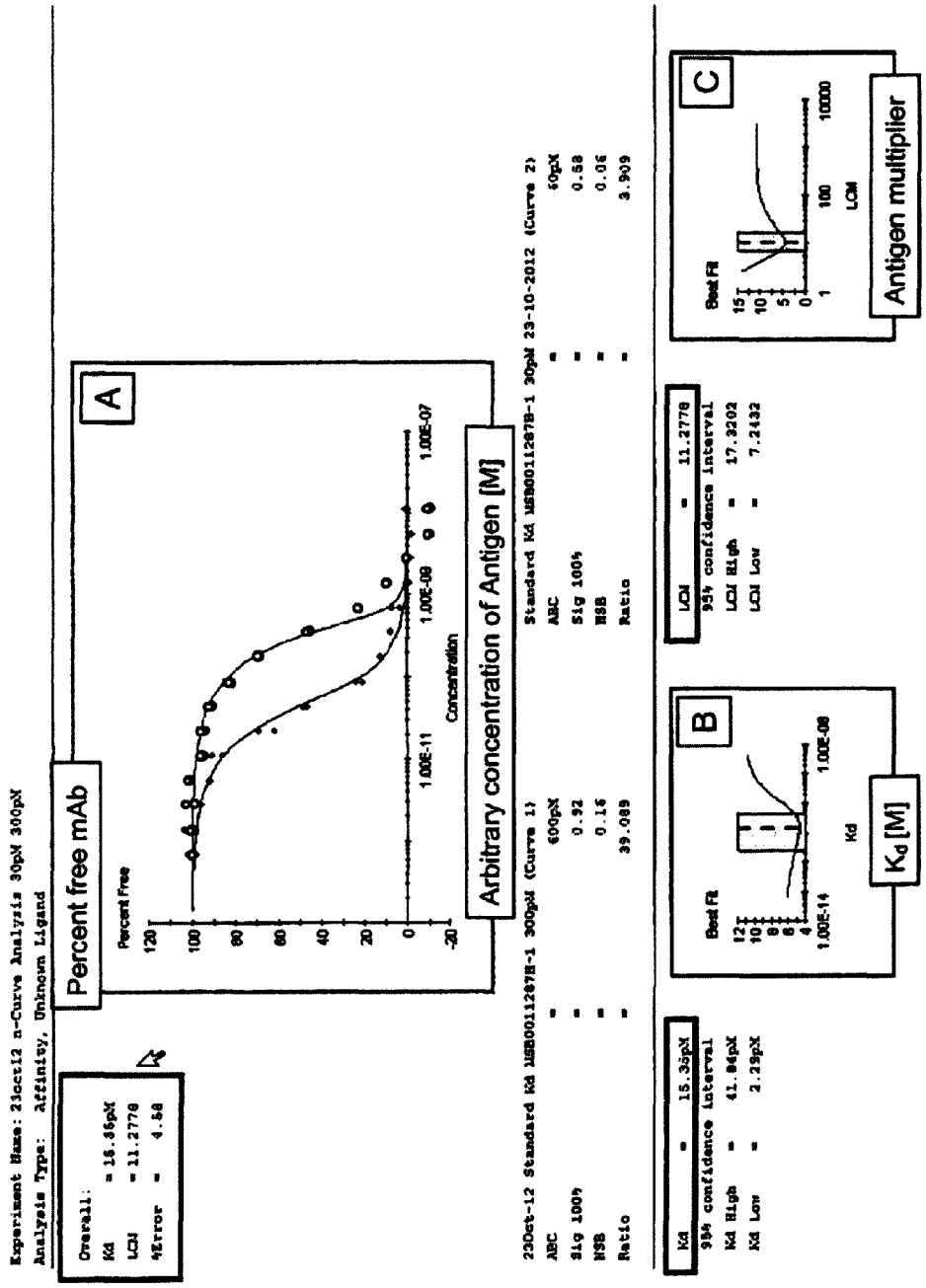

Representative experiments of Kd calculated by the KinExA software using n-curve analysis for 40C01-VH1-Vk3 and 40C01-VH2-Vk3 are shown in FIGS. 12 and 13, respectively. The Kd calculated for the human anti-CXCR5 mAb 40C01-VH1-Vk3 was 15.35 pM with Kd high of 41.84 pM and Kd low of 2.29 pM at 95% confidence intervals. Antigen multiplier of 11.3 was calculated by this method which translates to $1.6 \times 10^5$ CXCR5 receptors per cell. The Kd calculated for the human anti-CXCR5 mAb 40C01-VH2-Vk3 was 47.04 pM with Kd high of 92.41 pM and Kd low of 20.44 pM at 95% confidence intervals. Antigen multiplier of 22.94 was calculated by this method which translates to $2.8\ 10^6$ CXCR5 receptors per cell.

2.10. Anti-CXCR5 40C01-VH1-Vk2-Mediated ADCC.

Figure 14:
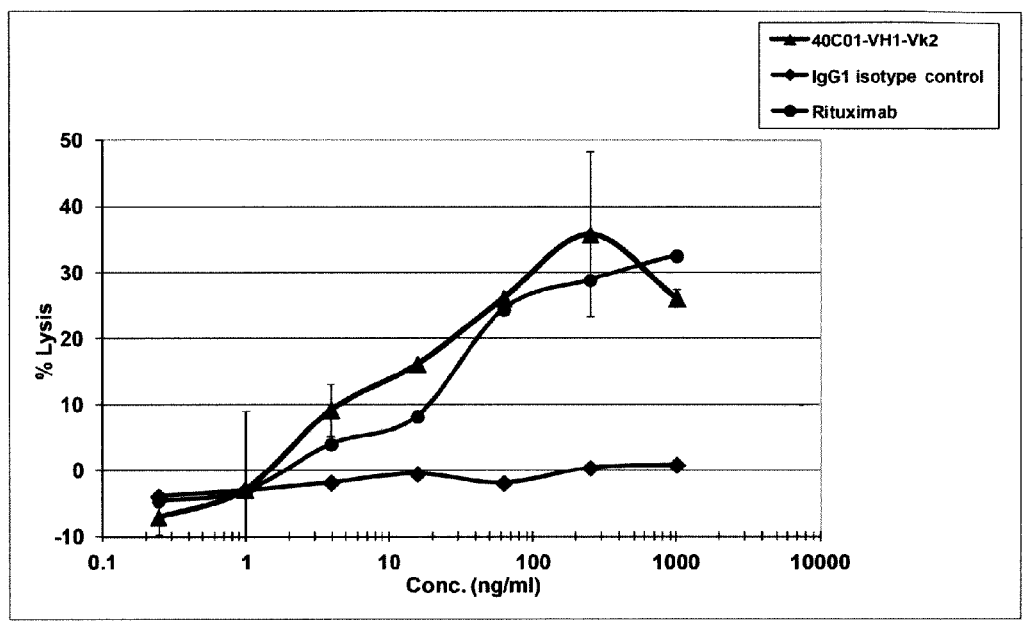

Antibody-dependent cell-mediated cytotoxicity (ADCC) assays against chromium-51-labelled target cells were performed using human B cells as target and human NK cells as effector cells. B cells and NK cells were purified from human PBMCs using respective MACS cells isolation kits from Miltenyi Biotec. Isolated B cells were then labelled with 51Cr. To measure cytotoxicity, effector (E) and target (T) cells at a 10/1 E/T ratio, were coincubated with anti-CXCR5-40C01-VH1-Vk2 mAb, rituximab (positive control IgG1 mAb), anti-Hen-Egg-Lysozyme mAb (negative control IgG1 mAb) or medium alone at 37° C. for 4 hrs. The percentage of cytolysis was calculated using the formula: percentage of specific lysis=((experimental counts per minute (c.p.m.)−spontaneous c.p.m.)/(maximal c.p.m.−spontaneous c.p.m.))×100. The results presented in FIG. 14 show that anti-CXCR5 40C01-VH1-Vk2 mAb has the capacity to mediate ADCC against primary human B cells and that its efficacy is as good as if not better than that of the well documented FDA approved anti-CD20 antibody, rituximab.

2.11. Afucosylated Anti-CXCR5 40C01-VH1-Vk3-IgG1-Mediated ADCC

Antibody-dependent cell-mediated cytotoxicity (ADCC) assays against chromium-51-labelled target cells were performed using as target cells the L1.2 cells stably expressing either human or cynomologous monkey (*Macaca fascicularis*) CXCR5 (see example 1.7 above) and human PBMCs as effector cells. To measure cytotoxicity, effector (E) and target (T) cells at a 100/1 E/T ratio, were coincubated with anti-CXCR5-40C01-VH1-Vk3-IgG1 mAb, anti-CXCR5-40C01-VH1-Vk3-IgG1_low_fucose mAb or medium alone at 37° C. for 4 hrs. The percentage of cytolysis was calculated using the formula: percentage of specific lysis=((experimental counts per minute (c.p.m.)−spontaneous c.p.m.)/(maximal c.p.m.−spontaneous c.p.m.))×100. The results presented in FIG. 15 show that anti-CXCR5-40C01-VH1-Vk3-IgG1 mAb has the capacity to mediate ADCC against L1.2 target cells expressing either human or cynomologous monkey CXCR5. Furthermore, that under the same assay conditions the afucosylated version of this antibody (anti-CXCR5-40C01-VH1-Vk3-IgG1_low_fucose) displayed enhanced ADCC activity against target cells expressing either human or cynomologous monkey CXCR5.

2.12. Anti-CXCR5 40C01-VH1-Vk3-IgG1 Induces Depletion of Human B Cells

Human PBMCs from 5 donors were cultured in the presence of anti-CXCR5 antibodies or an IgG1 isotype control antibody over a range of concentrations. After an overnight incubation, the percentage of CD19+ B cells among the lymphocyte population was assessed by flow cytometry. The data was normalized to the isotype control and combined from each donor. As shown in FIG. 16, we observed that 40C01-VH1-Vk3-IgG2_DI-NQ-HC2h did not cause depletion of B cells. However, both the 40C01-VH1-Vk3-IgG1 and 40C01-VH1-Vk3-IgG1_low_fucose versions did cause depletion of human B cells. We found that the 40C01-VH1-Vk3-IgG1_low_fucose version was more potent, as lower amounts of this antibody were needed to induce B cell depletion. These data demonstrate that 40C01-VH1-Vk3-IgG1 and 40C01-VH1-Vk3-IgG1_low_fucose can induce depletion of human B cells, with 40C01-VH1-Vk3-IgG1_low_fucose having enhanced potency.

TABLE 1

Table summarizing the $IC_{50}$ values of various mAbs of the invention

| Clone ID. | Mean $IC_{50}$ (nM) on L1.2/human CXCR5 cells |
|---|---|
| 40C01 | 5.6 |
| 80A11 | 1.85 |
| 80A10 | 4.7 |
| 42F03 | 1.86 |
| 80D11 | 37 |
| 80B09 | 251 |
| 12A01 | 2200 |

TABLE 2

Table summarizing the $IC_{50}$ values obtained from FIG. 5
Inhibition of CXCL13-induced L1.2-CXCR5 chemotaxis
Anti-CXCR5 40C01 fully human mAb variants

| Human IgG isotype | VH1-Vk3 | VH2-Vk3 | VH1-Vk3 | VH2-Vk3 |
|---|---|---|---|---|
| | $IC_{50}$ nM | | | |
| | Human | | Cynomolgus | |
| 4 | 2.1 | 0.103 | Not tested | |
| 2 | 1.15 | 0.108 | Not tested | |
| 1 | 1.81 | 0.098 | 0.19 | 0.17 |

Figure 11A:
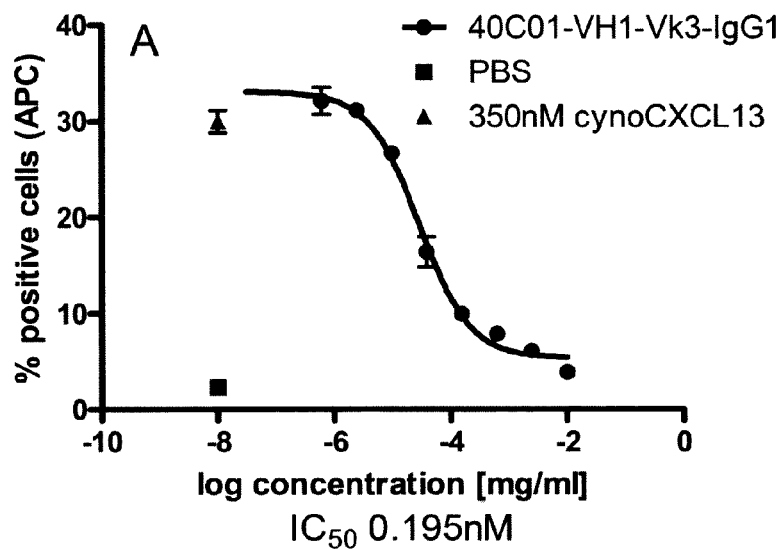
Figure 11B:
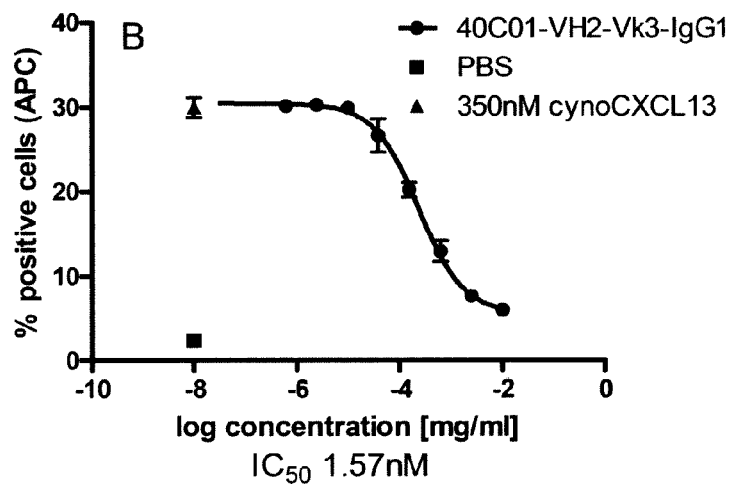

TABLE 3 table summarizing the $IC_{50}$ values obtained from FIG. 10 and 11.
Inhibition of ERK phosphorylation in whole blood
Anti-CXCR5 40C01 fully human mAb variants

| Human IgG isotype | VH1-Vk3 | VH2-Vk3 | VH1-Vk3 | VH2-Vk3 |
|---|---|---|---|---|
| | $IC_{50}$ nM | | | |
| | Human | | Cynomolgus | |
| 1 | 0.17 | 0.45 | Not tested | |
| 2 | 0.736 | 0.88 | 0.195 | 1.57 |

REFERENCES

1) Kabat et al. (1991) Sequences of Proteins of Immunological Interest. 5th Ed. Public Health Service, National Institutes of Health, Bethesda, Md.
2) Chothia and Lesk, (1987) J. Mol. Bioi., 196: 901-917.
3) Chirgwin J M et al. (1979) Biochemistry, 18(24): 5294-9.
4) Aviv H et al. (1972) Proc Natl Acad Sci USA, 69(6): 1408-12.
5) Harris J M et al. (2003) Nat Rev Drug Discov., 2(3): 214-221
6) Francis G E et al. (1998) Int. J Hematol., 68(1): 1-18.
7) Mirzabekov et al., (2000) Please add the info of publication
8) Hoet et al., (2005) Please add the info of publication
9) Angal et al. (1993) Mol. Immunol. 30:105-108
10) Ionescu et al. (2008) J Pharm Sci, 97:1414-1426, 2008
11) Hausdorff et al. (1990) FASEB J. 4:2881-2889.
12) Tomhave et al. (1994) J Immunol. 153:3267-3275
13) Press and Hogg (1970) Biochem J. 117: 641-660
14) Burkle et al. (2007) Blood. 110:3316-33251
15) WO2009032661
16) WO2009010290
17) F. Nimmerjahn, et al (2011) Curr. Top. Microbiol. Immunol., 350:105-125

The invention claimed is:

1. A monoclonal antibody, or an antigen-binding fragment thereof, that binds to CXCR5, which comprises:
   a) a heavy chain variable domain comprising H-CDR1, H-CDR2 and H-CDR3, wherein:
      i) H-CDR1 comprises SEQ ID NO: 8 or 9;
      ii) H-CDR2 comprises SEQ ID NO: 10 or 11; and
      iii) H-CDR3 comprises SEQ ID NO: 12 or 13; and
   b) a light chain variable domain comprising L-CDR1 L-CDR2 and L-CDR3, wherein:
      i) L-CDR1 comprises SEQ ID NO: 14 or 15;
      ii) L-CDR2 comprises SEQ ID NO: 16 or 17; and
      iii) L-CDR3 comprises SEQ ID NO: 18 or 19.

2. The monoclonal antibody according to claim 1, wherein:
   a) H-CDR1, H-CDR2 and H-CDR3 comprise:
      i) amino acid sequences SEQ ID NOs: 8, 10 and 12;
      ii) amino acid sequences SEQ ID NOs: 8, 11 and 12; or
      iii) amino acid sequences SEQ ID NOs: 9, 11 and 13; and
   b) L-CDR1, L-CDR2 and L-CDR3 comprise:
      i) amino acid sequences SEQ ID NOs: 14, 16 and 18;
      ii) amino acid sequences SEQ ID NOs: 15, 17 and 18; or
      iii) amino acid sequences SEQ ID NOs: 15, 17 and 19.

3. The monoclonal antibody according to claim 1, wherein:
   a) the heavy chain variable domain further comprises Framework Regions H-FR1, H-FR2, H-FR3 and H-FR4, wherein:
      i) H-FR1 comprises SEQ ID NO: 20;
      ii) H-FR2 comprises SEQ ID NO: 21 or 22;
      iii) H-FR3 comprises SEQ ID NO: 23 or 24; and
      iv) H-FR4 comprises SEQ ID NO: 25; and
   b) the light chain variable domain further comprises Framework regions L-FR1, L-FR2, L-FR3 and L-FR4, wherein:
      i) L-FR1 comprises SEQ ID NO: 26, 27 or 28;
      ii) L-FR2 comprises SEQ ID NO: 29, 30 or 31;
      iii) L-FR3 comprises SEQ ID NO: 32 or 33; and
      iv) L-FR4 comprises SEQ ID NO: 34.

4. The monoclonal antibody according to claim 3, wherein:
   a) H-FR1, H-FR2, H-FR3 and H-FR4 comprise:
      i) amino acid sequences SEQ ID NOs: 20, 21, 23 and 25; or
      ii) amino acid sequences SEQ ID NOs: 20, 22, 24 and 25; and
   b) L-FR1, L-FR2, L-FR3 and L-FR4 comprise:
      i) amino acid sequences SEQ ID NOs: 26, 29, 32 and 34;
      ii) amino acid sequences SEQ ID NOs: 27, 30, 33 and 34; or
      iii) amino acid sequences SEQ ID NOs: 28, 31, 33 and 34.

5. The monoclonal antibody according to claim 1, wherein:
   a) the heavy chain variable domain comprises an amino acid sequence selected from the group consisting of SEQ ID NOs: 1, 3 and 4; and
   b) the light chain variable domain comprises an amino acid sequence selected from the group consisting of SEQ ID NOs: 2, 5, 6 and 7.

6. The monoclonal antibody according to claim 1, wherein said monoclonal antibody comprises a heavy chain constant region, said constant region being selected from IgG1, IgG2, IgG3 or IgG4.

7. A pharmaceutical composition comprising a monoclonal antibody according to claim 1.

8. A polynucleotide encoding the heavy chain of the monoclonal antibody, or an antigen-binding fragment thereof, according to claim 1.

9. A polynucleotide encoding the light chain of the monoclonal antibody, or an antigen-binding fragment thereof, according to claim 1.

10. A polynucleotide encoding both the heavy chain and the light chain of the monoclonal antibody, or an antigen-binding fragment thereof, according to claim 1.

11. An expression vector comprising a polynucleotide according to claim 8.

12. An expression vector comprising a polynucleotide according to claim 9.

13. An expression vector comprising a polynucleotide according to claim 10.

14. An isolated host cell transformed with one or more expression vectors encoding an antibody according to claim 1.

15. The host cell of claim 14, wherein said host cell is transformed with a first expression vector comprising a polynucleotide encoding the light chain of said antibody and a second expression vector comprising a polynucleotide encoding the heavy chain of said antibody.

16. The host cell of claim 14, wherein said host cell is transformed with an expression vector comprising a polynucleotide encoding the light chain of said antibody and an expression vector comprising a polynucleotide encoding the heavy chain of said antibody.

17. The host cell according to claim 14, wherein said cell is a mammalian cell.

18. A composition comprising an isolated host cell according to claim 14 and culture medium.

19. A method for producing a monoclonal antibody comprising the steps of:
   a) culturing a host cell according to claim 14; and
   b) isolating said antibody produced by the host cell.

20. A method of treating an autoimmune disease, inflammatory disease, or cancer comprising the administration of a monoclonal antibody according to claim 1 in an amount effective to treat a patient having an autoimmune disease, inflammatory disease, or cancer.

\* \* \* \* \*

UNITED STATES PATENT AND TRADEMARK OFFICE
CERTIFICATE OF CORRECTION

PATENT NO. : 9,534,054 B2
APPLICATION NO. : 14/787478
DATED : January 3, 2017
INVENTOR(S) : Christine Power et al.

Page 1 of 1

It is certified that error appears in the above-identified patent and that said Letters Patent is hereby corrected as shown below:

In the Specification

Column 28,
Line 43, "100 μM" should read --100 pM--.
Line 54, "30 μM" should read --30 pM--.
Line 55, "100 μM" should read --100 pM--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*